United States Patent
Schuh et al.

(10) Patent No.: US 9,713,509 B2
(45) Date of Patent: Jul. 25, 2017

(54) INSTRUMENT DEVICE MANIPULATOR WITH BACK-MOUNTED TOOL ATTACHMENT MECHANISM

(71) Applicant: Auris Surgical Robotics, Inc., San Carlos, CA (US)

(72) Inventors: Travis Schuh, Los Altos, CA (US); Matthew Reagan Williams, Walnut Creek, CA (US); Joseph Daniel Bogusky, San Jose, CA (US); David S. Mintz, Mountain View, CA (US); Alan Yu, Union City, CA (US); Yoichiro Dan, Mountain View, CA (US)

(73) Assignee: Auris Surgical Robotics, Inc., San Carlos, CA (US)

( * ) Notice: Subject to any disclaimer, the term of this patent is extended or adjusted under 35 U.S.C. 154(b) by 0 days.

(21) Appl. No.: 15/261,753

(22) Filed: Sep. 9, 2016

(65) Prior Publication Data

US 2017/0065363 A1     Mar. 9, 2017

Related U.S. Application Data

(60) Provisional application No. 62/216,239, filed on Sep. 9, 2015.

(51) Int. Cl.
*A61B 34/30* (2016.01)
*A61B 90/50* (2016.01)
(Continued)

(52) U.S. Cl.
CPC .............. *A61B 90/50* (2016.02); *A61B 34/00* (2016.02); *A61B 34/30* (2016.02); *A61B 34/70* (2016.02); *A61B 46/00* (2016.02); *A61B 46/10* (2016.02)

(58) Field of Classification Search
CPC .............. A61B 34/30–2034/303; A61B 90/50
(Continued)

(56) References Cited

U.S. PATENT DOCUMENTS 2,566,183 A    8/1951 Forss
2,730,699 A    1/1956 Gratian
(Continued)

FOREIGN PATENT DOCUMENTS

EP    2392435 A2    12/2011
JP    H09224951 A    9/1997
(Continued)

OTHER PUBLICATIONS

PCT Invitation to Pay Additional Fees, PCT Application No. PCT/US2016/051154, Oct. 21, 2016, 2 pages.
(Continued)

*Primary Examiner* — Zade Coley
(74) *Attorney, Agent, or Firm* — Knobbe, Martens, Olson & Bear, LLP

(57) ABSTRACT

An instrument device manipulator (IDM) is attached to a surgical arm of a robotic system and comprises a surgical tool holder and an outer housing. The surgical tool holder includes an attachment interface that can secure a surgical tool in a front-mount configuration (where the attachment interface is on a face opposite of an elongated body of the surgical tool) or a back-mount configuration (where the attachment interface is on the same face as the elongated body of the surgical tool). The surgical tool holder may rotate continuously within the outer housing. In a back-mount configuration, the surgical tool holder may have a passage that receives the elongated body of the tool and allows free rotation of the elongated body about the rota-
(Continued)

tional axis. A surgical drape separates the IDM and robotic arm from a tool, while allowing electrical and/or optical signals to pass therebetween.

19 Claims, 19 Drawing Sheets

(51) Int. Cl.
*A61B 34/00* (2016.01)
*A61B 46/00* (2016.01)
*A61B 46/10* (2016.01)

(58) Field of Classification Search
USPC .......................................................... 606/185
See application file for complete search history.

(56) References Cited

U.S. PATENT DOCUMENTS

| | | | |
|---|---|---|---|
| 3,472,083 A | 10/1969 | Schnepel |
| 4,357,843 A | 11/1982 | Peck et al. |
| 4,597,388 A | 7/1986 | Koziol et al. |
| 4,784,150 A | 11/1988 | Voorhies et al. |
| 4,905,673 A | 3/1990 | Pimiskern |
| 4,945,790 A | 8/1990 | Golden |
| 5,207,128 A | 5/1993 | Albright |
| 5,234,428 A | 8/1993 | Kaufman |
| 5,277,085 A | 1/1994 | Tanimura et al. |
| 5,425,735 A | 6/1995 | Rosen et al. |
| 5,426,687 A | 6/1995 | Goodall et al. |
| 5,472,406 A | 12/1995 | De La Torre et al. |
| 5,572,999 A | 11/1996 | Funda et al. |
| 5,662,590 A | 9/1997 | De La Torre et al. |
| 5,695,500 A | 12/1997 | Taylor et al. |
| 5,792,135 A | 8/1998 | Madhani et al. |
| 5,855,583 A | 1/1999 | Wang et al. |
| 6,033,371 A | 3/2000 | Torre et al. |
| 6,326,616 B1 | 12/2001 | Andrien et al. |
| 6,398,792 B1 | 6/2002 | O'Connor |
| 6,401,572 B1 | 6/2002 | Provost |
| 6,406,486 B1 | 6/2002 | De La Torre et al. |
| 6,436,107 B1 | 8/2002 | Wang et al. |
| 6,487,940 B2 | 12/2002 | Hart et al. |
| 6,554,793 B1 | 4/2003 | Pauker et al. |
| 6,638,246 B1 | 10/2003 | Naimark et al. |
| 6,671,581 B2 | 12/2003 | Niemeyer et al. |
| 6,736,784 B1 | 5/2004 | Menne et al. |
| 6,763,259 B1 | 7/2004 | Hauger et al. |
| 6,827,712 B2 | 12/2004 | Tovey et al. |
| 7,087,061 B2 | 8/2006 | Chernenko et al. |
| 7,344,528 B1 | 3/2008 | Tu et al. |
| 7,351,193 B2 | 4/2008 | Forman et al. |
| 7,725,214 B2 | 5/2010 | Diolaiti |
| 7,883,475 B2 | 2/2011 | Dupont et al. |
| 7,967,799 B2 | 6/2011 | Boukhny |
| 8,049,873 B2 | 11/2011 | Hauger et al. |
| 8,224,484 B2 | 7/2012 | Swarup et al. |
| 8,291,791 B2 | 10/2012 | Light et al. |
| 8,414,564 B2 | 4/2013 | Goldshleger et al. |
| 8,518,024 B2 | 8/2013 | Williams et al. |
| 8,746,252 B2 | 6/2014 | McGrogan et al. |
| 9,204,933 B2 | 12/2015 | Reis et al. |
| 9,226,796 B2 | 1/2016 | Bowling et al. |
| 9,457,168 B2 | 10/2016 | Moll et al. |
| 2002/0045905 A1 | 4/2002 | Gerbi et al. |
| 2004/0030349 A1 | 2/2004 | Boukhny |
| 2004/0257021 A1 | 12/2004 | Chang et al. |
| 2005/0070844 A1 | 3/2005 | Chow et al. |
| 2005/0222714 A1 | 10/2005 | Nihei et al. |
| 2006/0253108 A1 | 11/2006 | Yu et al. |
| 2007/0013336 A1 | 1/2007 | Nowlin et al. |
| 2007/0032906 A1 | 2/2007 | Sutherland et al. |
| 2007/0135733 A1 | 6/2007 | Soukup et al. |
| 2007/0135763 A1 | 6/2007 | Musbach et al. |
| 2007/0299427 A1 | 12/2007 | Yeung et al. |
| 2008/0065103 A1 | 3/2008 | Cooper et al. |
| 2008/0065109 A1 | 3/2008 | Larkin |
| 2008/0097293 A1 | 4/2008 | Chin et al. |
| 2008/0114341 A1 | 5/2008 | Thyzel |
| 2008/0177285 A1 | 7/2008 | Brock et al. |
| 2008/0187101 A1 | 8/2008 | Gertner |
| 2008/0228104 A1 | 9/2008 | Uber et al. |
| 2008/0231221 A1 | 9/2008 | Ogawa |
| 2009/0171271 A1 | 7/2009 | Webster et al. |
| 2009/0248041 A1 | 10/2009 | Williams et al. |
| 2009/0248043 A1 | 10/2009 | Tierney et al. |
| 2009/0264878 A1 | 10/2009 | Carmel et al. |
| 2009/0268015 A1 | 10/2009 | Scott et al. |
| 2009/0287354 A1 | 11/2009 | Choi |
| 2009/0312768 A1 | 12/2009 | Hawkins et al. |
| 2009/0326322 A1 | 12/2009 | Diolaiti |
| 2010/0036294 A1 | 2/2010 | Mantell et al. |
| 2010/0073150 A1 | 3/2010 | Olson et al. |
| 2010/0256812 A1 | 10/2010 | Tsusaka et al. |
| 2011/0009779 A1 | 1/2011 | Romano et al. |
| 2011/0028887 A1 | 2/2011 | Fischer et al. |
| 2011/0040404 A1 | 2/2011 | Diolaiti et al. |
| 2011/0046441 A1 | 2/2011 | Wiltshire et al. |
| 2011/0106102 A1 | 5/2011 | Balicki et al. |
| 2011/0147030 A1 | 6/2011 | Blum et al. |
| 2011/0277775 A1 | 11/2011 | Holop et al. |
| 2011/0306836 A1 | 12/2011 | Ohline et al. |
| 2012/0071752 A1 | 3/2012 | Sewell et al. |
| 2012/0071821 A1 | 3/2012 | Yu |
| 2012/0138586 A1 | 6/2012 | Webster et al. |
| 2012/0186194 A1 | 7/2012 | Schlieper |
| 2012/0283747 A1 | 11/2012 | Popovic |
| 2013/0144116 A1 | 6/2013 | Cooper et al. |
| 2013/0325030 A1 | 12/2013 | Hourtash et al. |
| 2013/0345519 A1 | 12/2013 | Piskun et al. |
| 2014/0012276 A1 | 1/2014 | Alvarez |
| 2014/0069437 A1 | 3/2014 | Reis et al. |
| 2014/0135985 A1 | 5/2014 | Coste-Maniere et al. |
| 2014/0142591 A1 | 5/2014 | Alvarez et al. |
| 2014/0166023 A1 | 6/2014 | Kishi |
| 2014/0222019 A1 | 8/2014 | Brudniok |
| 2014/0222207 A1 | 8/2014 | Bowling et al. |
| 2014/0276594 A1 | 9/2014 | Tanner et al. |
| 2014/0296870 A1 | 10/2014 | Stern et al. |
| 2014/0296875 A1 | 10/2014 | Moll et al. |
| 2014/0309649 A1 | 10/2014 | Alvarez et al. |
| 2014/0364870 A1 | 12/2014 | Alvarez et al. |
| 2014/0379000 A1 | 12/2014 | Romo et al. |
| 2015/0025539 A1 | 1/2015 | Alvarez et al. |
| 2015/0051592 A1 | 2/2015 | Kintz |
| 2015/0090063 A1 | 4/2015 | Lantermann et al. |
| 2015/0101442 A1 | 4/2015 | Romo |
| 2015/0104284 A1 | 4/2015 | Riedel |
| 2015/0119638 A1 | 4/2015 | Yu et al. |
| 2015/0164594 A1 | 6/2015 | Romo et al. |
| 2015/0164595 A1 | 6/2015 | Bogusky et al. |
| 2015/0164596 A1 | 6/2015 | Romo et al. |
| 2015/0182250 A1 | 7/2015 | Conlon et al. |
| 2015/0342695 A1 | 12/2015 | He et al. |
| 2015/0359597 A1 | 12/2015 | Gombert et al. |
| 2015/0374445 A1 | 12/2015 | Gombert et al. |

FOREIGN PATENT DOCUMENTS

| | | |
|---|---|---|
| WO | WO 92/14411 A1 | 9/1992 |
| WO | WO 03/096871 A2 | 11/2003 |
| WO | WO 2004/105849 A1 | 12/2004 |
| WO | WO 2010/068005 A2 | 6/2010 |
| WO | WO 2011/161218 A1 | 12/2011 |

OTHER PUBLICATIONS

PCT International Search Report and Written Opinion, PCT Application No. PCT/US2016/051154, Jan. 10, 2017, 17 pages.
PCT International Search Report and Written Opinion, PCT Application No. PCT/US15/53306, Feb. 4, 2016, 19 pages.
European search report and search opinion dated Jul. 2, 2015 for EP Application No. 12856685.8.

(56) References Cited

OTHER PUBLICATIONS

Office action dated May 21, 2015 for U.S. Appl. No. 13/711,440.
Office action dated Jun. 11, 2015 for U.S. Appl. No. 14/158,548.
U.S. Appl. No. 14/578,082, filed Dec. 19, 2014, Inventor: Alvarez et al.
U.S. Appl. No. 14/583,021, filed Dec. 24, 2014, Inventor: Romo et al.
International search report and written opinion dated Jan. 27, 2015 for PCT Application No. US2014/062284.
U.S. Appl. No. 14/542,373, filed Nov. 14, 2014, Inventor: Romo et al.
U.S. Appl. No. 14/542,387, filed Nov. 14, 2014, Inventor: Bogusky et al.
U.S. Appl. No. 14/542,403, filed Nov. 14, 2014, Inventor: Yu et al.
U.S. Appl. No. 14/542,429, filed Nov. 14, 2014, Inventor: Romo et al.
Office action dated Oct. 7, 2014 for U.S. Appl. No. 13/711,440.
U.S. Appl. No. 14/196,953, filed Mar. 4, 2014.
U.S. Appl. No. 14/201,610, filed Mar. 7, 2014.
U.S. Appl. No. 14/301,871, filed Jun. 11, 2014.
U.S. Appl. No. 14/458,042, filed Aug. 12, 2014.
U.S. Appl. No. 14/479,095, filed Sep. 5, 2014.
U.S. Appl. No. 62/037,520, filed Aug. 14, 2014.
Balicki, et al. Single fiber optical coherence tomography microsurgical instruments for computer and robot-assisted retinal surgery. Medical Image Computing and Computer-Assisted Intervention. MICCAI 2009. Springer Berlin Heidelberg, 2009. 108-115.
Effect of Microsecond Pulse Length and Tip Shape on Explosive. Bubble Formation of 2.78 μm Er,Cr;YSGG and 2.94 μm Er:YAG Laser. Paper 8221-12, Proceedings of SPIE, vol. 8221 (Monday Jan. 23, 2013).
Ehlers, et al. Integration of a spectral domain optical coherence tomography system into a surgical microscope for intraoperative imaging. Investigative Ophthalmology and Visual Science 52.6. 2011; 3153-3159.
Hubschman. Robotic Eye Surgery: Past, Present, and Future. Journal of Computer Science and Systems Biology. 2012.
International search report and written opinion dated Mar. 29, 2013 for PCT/US2012/069540.
International search report and written opinion dated Nov. 7, 2014 for PCT Application No. US2014/041990.
International search report dated Jun. 16, 2014 for PCT/US2014/022424.
Office action dated Jun. 19, 2014 for U.S. Appl. No. 13/868,769.
Stoyanov. Surgical vision. Annals of Biomedical Engineering 40.2. 2012; 332-345. Published Oct. 20, 2011.

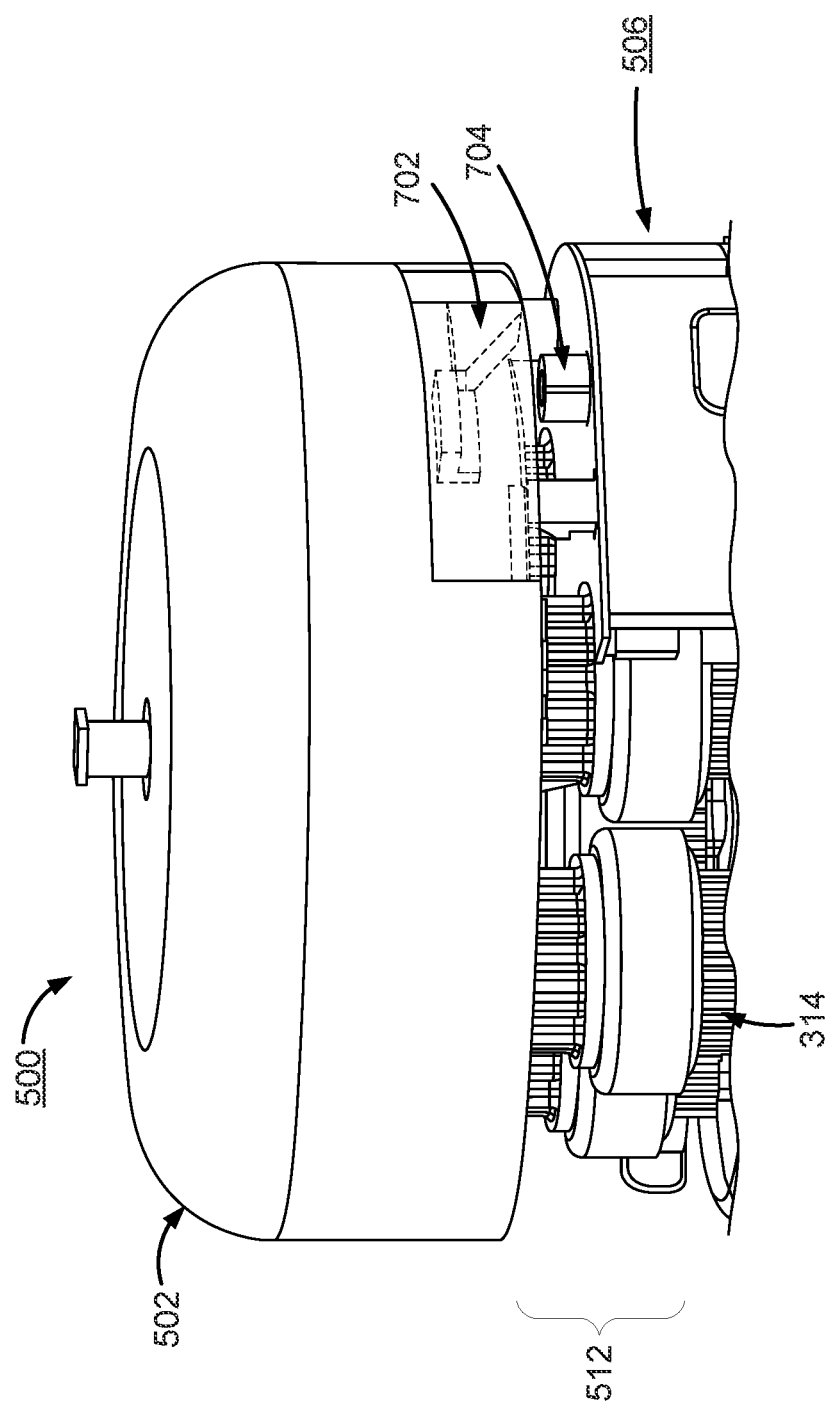

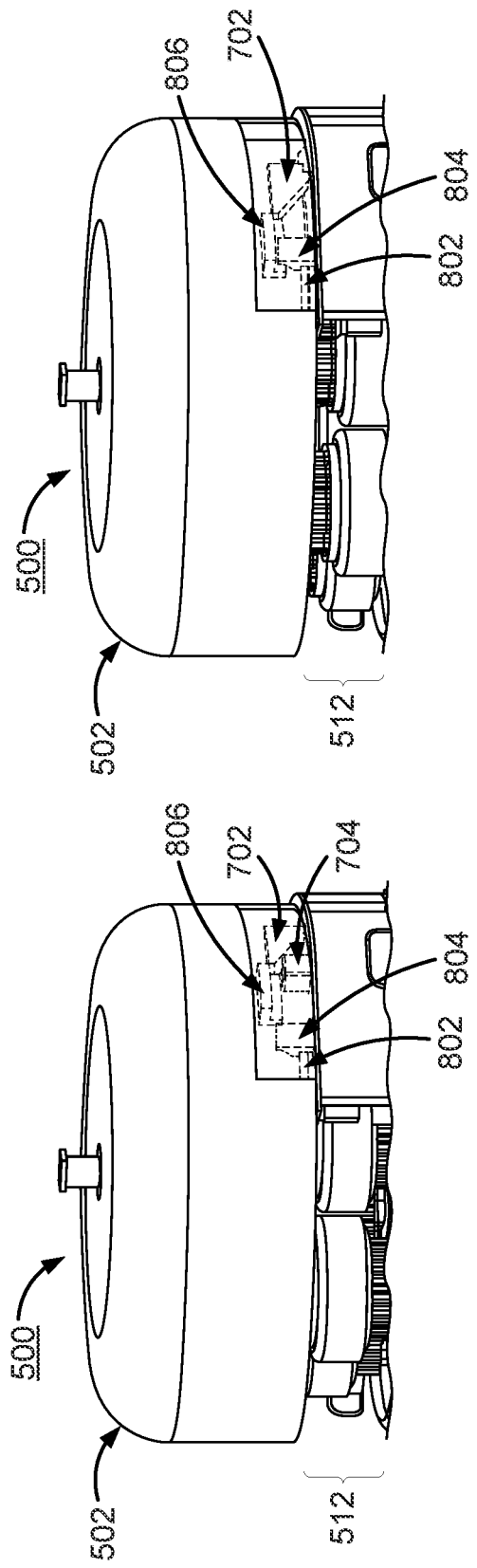

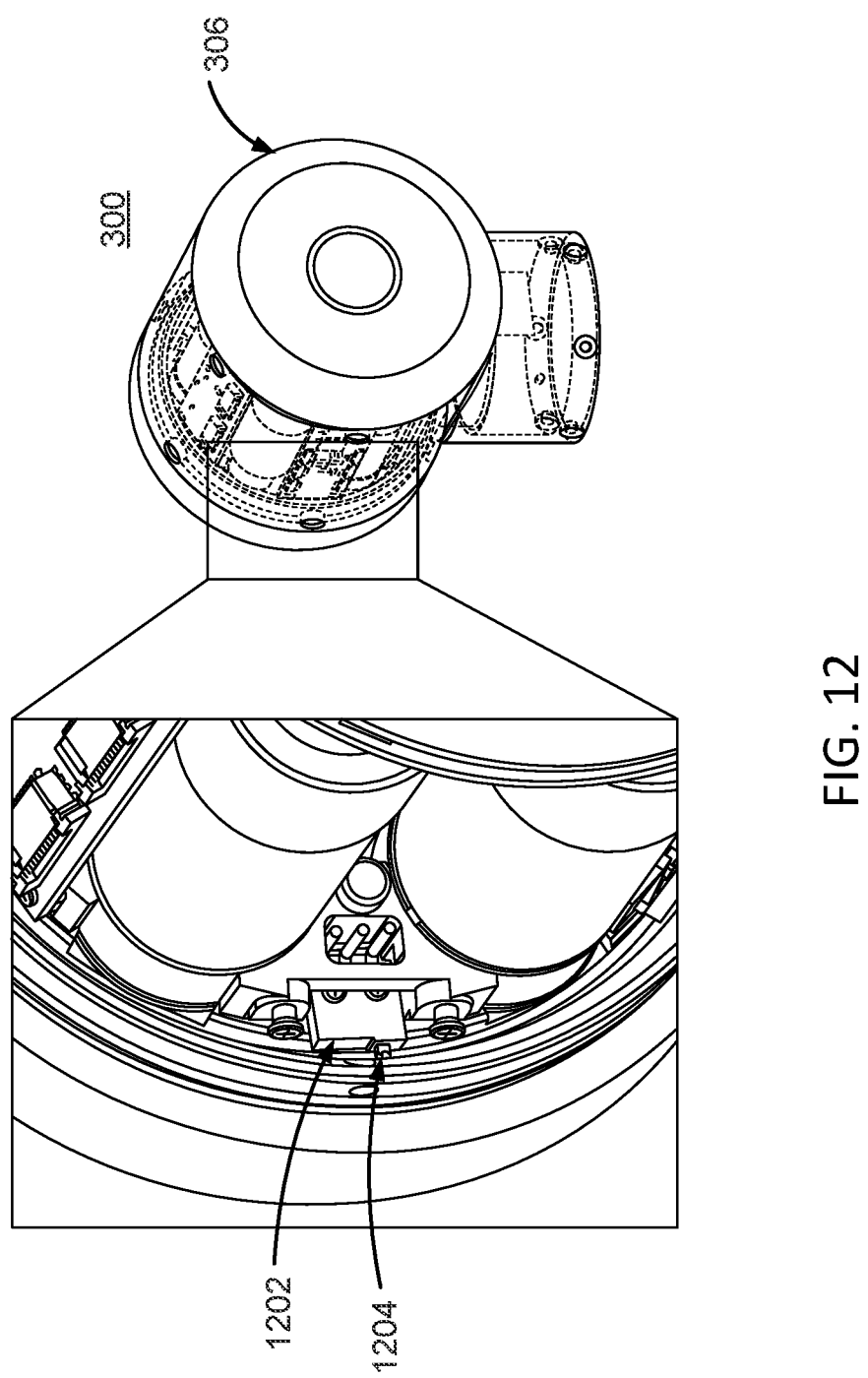

INSTRUMENT DEVICE MANIPULATOR WITH BACK-MOUNTED TOOL ATTACHMENT MECHANISM

CROSS-REFERENCE TO RELATED APPLICATIONS

This application claims the benefit of U.S. Provisional Application No. 62/216,239 filed Sep. 9, 2015, which is incorporated by reference herein in its entirety.

The subject matter of the present application is related to U.S. patent application Ser. No. 14/523,760, filed Oct. 24, 2014; U.S. patent application Ser. No. 14/542,403, filed Nov. 14, 2014 (which claims the benefit of U.S. Provisional Application No. 61/895,315, filed on Oct. 24, 2013); U.S. Provisional Application No. 62/019,816, filed Jul. 1, 2014; U.S. Provisional Patent Application No. 62/037,520, filed Aug. 14, 2014; U.S. Provisional Patent Application No. 62/057,936, filed Sep. 30, 2014; U.S. Provisional Patent Application No. 62/134,366, filed Mar. 17, 2015; and U.S. Provisional Patent Application No. 62/184,741, filed Jun. 25, 2015. Each of the foregoing is incorporated herein by reference in its entirety.

BACKGROUND

This description generally relates to surgical robotics, and particularly to an instrument device manipulator having a back-mounted attachment mechanism for a surgical tool.

Robotic technologies have a range of applications. In particular, robotic arms help complete tasks that a human would normally perform. For example, factories use robotic arms to manufacture automobiles and consumer electronics products. Additionally, scientific facilities use robotic arms to automate laboratory procedures such as transporting microplates. In the medical field, physicians have started using robotic arms to help perform surgical procedures.

In a surgical robotic system, a robotic arm is connected to an instrument device manipulator, e.g., at the end of the robotic arm, and is capable of moving the instrument device manipulator into any position within a defined work space. The instrument device manipulator can be detachably coupled to a surgical tool, such as a steerable catheter for endoscopic applications or any of a variety of laparoscopic tools. The instrument device manipulator imparts motion from the robotic arm to control the position of the surgical tool, and it may also activate controls on the tool, such as pull-wires to steer a catheter. Additionally, the instrument device manipulator may be electrically and/or optically coupled to the tool to provide power, light, or control signals, and may receive data from the tool such as a video stream from a camera on the tool.

During use, a surgical tool is connected to the instrument device manipulator so that the tool is away from a patient, and the robotic arm then advances the instrument device manipulator and the tool connected thereto towards a surgery site within the patient. In some situations during a surgery, it may be desirable to quickly disconnect the tool from the instrument device manipulator and remove it from the patient. But when the tool is connected to a distal face of the instrument device manipulator, removing the tool from the instrument device manipulator may require advancing the tool a small distance towards the surgical site so that the tool can be lifted off of the attachment mechanism of the instrument device manipulator. Even a slight motion towards the surgical site may cause damage to a patient. Alternatively, the surgical tool may be connected to a top face of the instrument device manipulator. Although this may allow the tool to be disconnected from the instrument device manipulator without advancing the tool towards the surgical site, connecting the tool in a way that is not symmetrical about an axis of the tool may limit the amount of roll that the surgical arm and/or instrument device manipulator can impart to the tool.

SUMMARY

Embodiments of the invention enable a surgical tool to be disconnected from an instrument device manipulator on a robotic arm of a surgical robotic system without advancing the tool towards a surgery site. For example, an attachment mechanism is included on a proximal face of the instrument device manipulator (away from the patient) so that the motion required to move the tool sufficiently to clear any attachment mechanism of the instrument device manipulator is in a direction away from the surgical site, thereby withdrawing a distal end of the tool from the surgery site. Moreover, the instrument device manipulator may also include a passageway therethrough to allow the tool to attach to the instrument device manipulator in a way that is generally symmetrical about an axis of the tool. As opposed to a side-mounted scheme, this allows for a greater amount of roll (possibly infinite) to be imparted to the tool by the instrument device manipulator.

In various embodiments, a surgical instrument manipulation system comprises a surgical arm, a surgical tool holder assembly, and a surgical tool. The surgical tool holder assembly can be attached to the surgical tool via an attachment interface on the surgical tool holder. The surgical tool holder assembly further comprises a passage that receives an elongated body of the surgical tool. The attachment interface includes one or more torque couplers, which can engage with a plurality of instrument inputs on the surgical tool. The torque couplers are driven by actuators that cause the torque couplers to rotate, thereby rotating the plurality of instrument inputs and thus driving a plurality of end-effectors of the surgical tool. The attachment interface further comprises an attachment mechanism that releasably secures the surgical tool and the surgical tool holder assembly. This configuration allows a surgical tool to be removed from the surgical tool holder assembly in a distal direction to a patient, improving patient safety during surgical tool removal.

In certain embodiments, the surgical tool holder assembly can continuously rotate or "roll" about a rotational axis that is co-axially aligned with the passage. This configuration allows free rotation of the surgical tool about a rotational axis and the elongated body of the surgical tool attached to the surgical tool holder assembly.

BRIEF DESCRIPTION OF DRAWINGS

FIG. 7 illustrates a zoomed-in, perspective view of an actuation mechanism for engagement and disengagement of a surgical tool from a surgical tool holder, according to one embodiment.

FIGS. 8A and 8B illustrate a process of engaging and disengaging a surgical tool from a sterile adapter, according to one embodiment.

FIG. 12 illustrates a zoomed-in, perspective view of electrical components of an instrument device manipulator for roll indexing the surgical tool holder, according to one embodiment.

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

I. Surgical Robotic System

Figure 1:
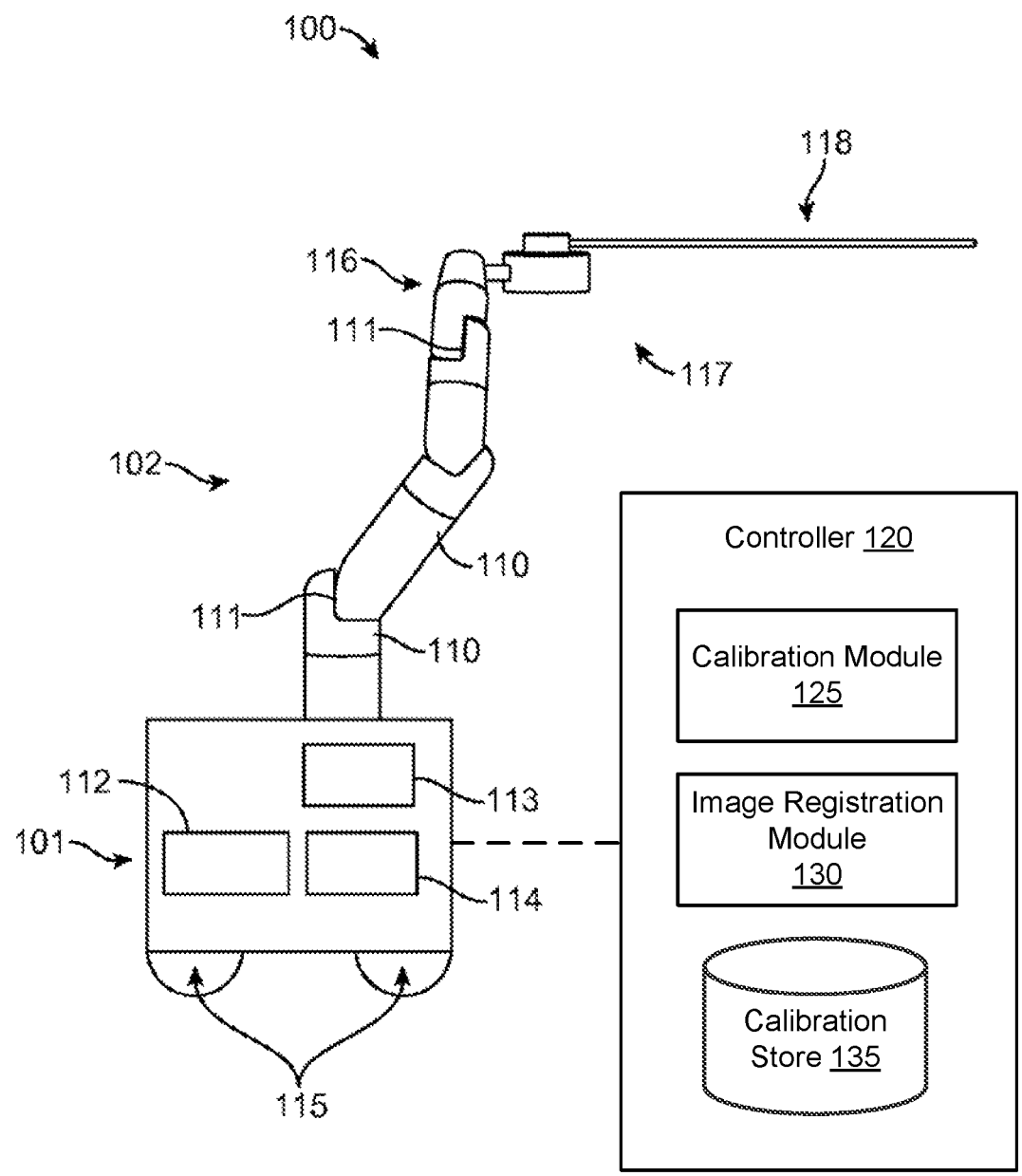
FIG. 1 illustrates a surgical robotic system, according to one embodiment.

FIG. 1 illustrates an embodiment of a surgical robotic system 100. The surgical robotic system 100 includes a base 101 coupled to one or more robotic arms, e.g., robotic arm 102. The base 101 is communicatively coupled to a command console, which is further described herein with reference to FIG. 2. The base 101 can be positioned such that the robotic arm 102 has access to perform a surgical procedure on a patient, while a user such as a physician may control the surgical robotic system 100 from the comfort of the command console. In some embodiments, the base 101 may be coupled to a surgical operating table or bed for supporting the patient. Though not shown in FIG. 1 for purposes of clarity, the base 101 may include subsystems such as control electronics, pneumatics, power sources, optical sources, and the like. The robotic arm 102 includes multiple arm segments 110 coupled at joints 111, which provides the robotic arm 102 multiple degrees of freedom, e.g., seven degrees of freedom corresponding to seven arm segments. The base 101 may contain a source of power 112, pneumatic pressure 113, and control and sensor electronics 114—including components such as a central processing unit, data bus, control circuitry, and memory—and related actuators such as motors to move the robotic arm 102. The electronics 114 in the base 101 may also process and transmit control signals communicated from the command console.

In some embodiments, the base 101 includes wheels 115 to transport the surgical robotic system 100. Mobility of the surgical robotic system 100 helps accommodate space constraints in a surgical operating room as well as facilitate appropriate positioning and movement of surgical equipment. Further, the mobility allows the robotic arms 102 to be configured such that the robotic arms 102 do not interfere with the patient, physician, anesthesiologist, or any other equipment. During procedures, a user may control the robotic arms 102 using control devices such as the command console.

In some embodiments, the robotic arm 102 includes set up joints that use a combination of brakes and counter-balances to maintain a position of the robotic arm 102. The counter-balances may include gas springs or coil springs. The brakes, e.g., fail safe brakes, may include mechanical and/or electrical components. Further, the robotic arms 102 may be gravity-assisted passive support type robotic arms.

Each robotic arm 102 may be coupled to an instrument device manipulator (IDM) 117 using a mechanism changer interface (MCI) 116. The IDM 117 can be removed and replaced with a different type of IDM, for example, a first type of IDM manipulates an endoscope, while a second type of IDM manipulates a laparoscope. The MCI 116 includes connectors to transfer pneumatic pressure, electrical power, electrical signals, and optical signals from the robotic arm 102 to the IDM 117. The MCI 116 can be a set screw or base plate connector. The IDM 117 manipulates surgical instruments such as the endoscope 118 using techniques including direct drive, harmonic drive, geared drives, belts and pulleys, magnetic drives, and the like. The MCI 116 is interchangeable based on the type of IDM 117 and can be customized for a certain type of surgical procedure. The robotic 102 arm can include a joint level torque sensing and a wrist at a distal end, such as the KUKA AG® LBR5 robotic arm.

The endoscope 118 is a tubular and flexible surgical instrument that is inserted into the anatomy of a patient to capture images of the anatomy (e.g., body tissue). In particular, the endoscope 118 includes one or more imaging devices (e.g., cameras or sensors) that capture the images. The imaging devices may include one or more optical components such as an optical fiber, fiber array, or lens. The optical components move along with the tip of the endoscope 118 such that movement of the tip of the endoscope 118 results in changes to the images captured by the imaging devices. While an endoscope is used as the primary example throughout, it is understood that the surgical robotic system 100 may be used with a variety of surgical instruments.

In some embodiments, robotic arms 102 of the surgical robotic system 100 manipulate the endoscope 118 using elongate movement members. The elongate movement members may include pull-wires, also referred to as pull or push wires, cables, fibers, or flexible shafts. For example, the robotic arms 102 actuate multiple pull-wires coupled to the endoscope 118 to deflect the tip of the endoscope 118. The pull-wires may include both metallic and non-metallic materials such as stainless steel, Kevlar, tungsten, carbon fiber, and the like. The endoscope 118 may exhibit nonlinear behavior in response to forces applied by the elongate movement members. The nonlinear behavior may be based on stiffness and compressibility of the endoscope 118, as well as variability in slack or stiffness between different elongate movement members.

The surgical robotic system 100 includes a controller 120, for example, a computer processor. The controller 120 includes a calibration module 125, image registration module 130, and a calibration store 135. The calibration module 125 can characterize the nonlinear behavior using a model with piecewise linear responses along with parameters such as slopes, hystereses, and dead zone values. The surgical robotic system 100 can more accurately control an endoscope 118 by determining accurate values of the parameters. In some embodiments, some or all functionality of the controller 120 is performed outside the surgical robotic system 100, for example, on another computer system or server communicatively coupled to the surgical robotic system 100.

II. Command Console

Figure 2:
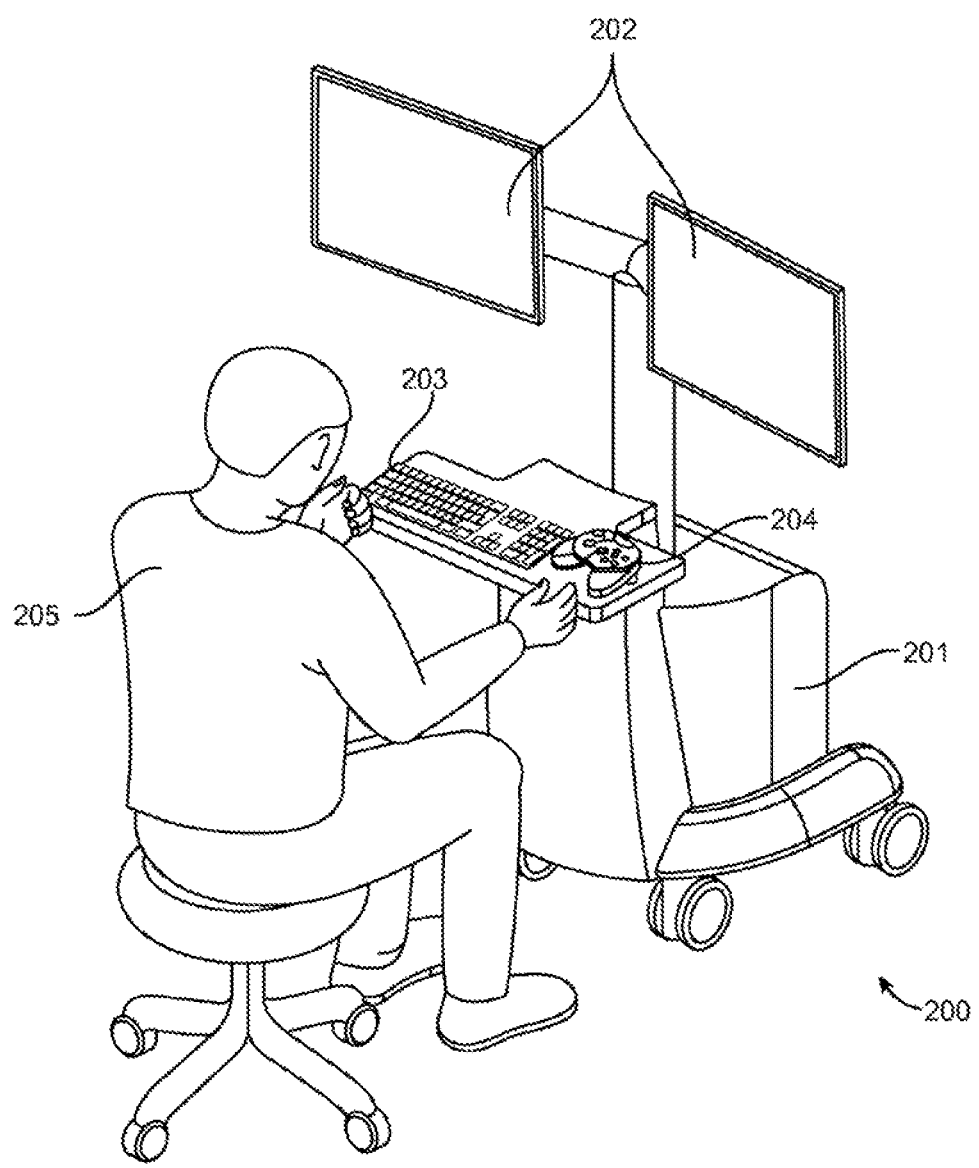
FIG. 2 illustrates a command console for a surgical robotic system, according to one embodiment.

FIG. 2 illustrates a command console 200 for a surgical robotic system 100 according to one embodiment. The command console 200 includes a console base 201, display modules 202, e.g., monitors, and control modules, e.g., a keyboard 203 and joystick 204. In some embodiments, one or more of the command module 200 functionality may be integrated into a base 101 of the surgical robotic system 100 or another system communicatively coupled to the surgical robotic system 100. A user 205, e.g., a physician, remotely controls the surgical robotic system 100 from an ergonomic position using the command console 200.

The console base 201 may include a central processing unit, a memory unit, a data bus, and associated data communication ports that are responsible for interpreting and processing signals such as camera imagery and tracking sensor data, e.g., from the endoscope 118 shown in FIG. 1. In some embodiments, both the console base 201 and the base 101 perform signal processing for load-balancing. The console base 201 may also process commands and instructions provided by the user 205 through the control modules 203 and 204. In addition to the keyboard 203 and joystick 204 shown in FIG. 2, the control modules may include other devices, for example, computer mice, track pads, trackballs, control pads, video game controllers, and sensors (e.g., motion sensors or cameras) that capture hand gestures and finger gestures.

The user 205 can control a surgical instrument such as the endoscope 118 using the command console 200 in a velocity mode or position control mode. In velocity mode, the user 205 directly controls pitch and yaw motion of a distal end of the endoscope 118 based on direct manual control using the control modules. For example, movement on the joystick 204 may be mapped to yaw and pitch movement in the distal end of the endoscope 118. The joystick 204 can provide haptic feedback to the user 205. For example, the joystick 204 vibrates to indicate that the endoscope 118 cannot further translate or rotate in a certain direction. The command console 200 can also provide visual feedback (e.g., pop-up messages) and/or audio feedback (e.g., beeping) to indicate that the endoscope 118 has reached maximum translation or rotation.

In position control mode, the command console 200 uses a three-dimensional (3D) map of a patient and pre-determined computer models of the patient to control a surgical instrument, e.g., the endoscope 118. The command console 200 provides control signals to robotic arms 102 of the surgical robotic system 100 to manipulate the endoscope 118 to a target location. Due to the reliance on the 3D map, position control mode requires accurate mapping of the anatomy of the patient.

In some embodiments, users 205 can manually manipulate robotic arms 102 of the surgical robotic system 100 without using the command console 200. During setup in a surgical operating room, the users 205 may move the robotic arms 102, endoscopes 118, and other surgical equipment to access a patient. The surgical robotic system 100 may rely on force feedback and inertia control from the users 205 to determine appropriate configuration of the robotic arms 102 and equipment.

The display modules 202 may include electronic monitors, virtual reality viewing devices, e.g., goggles or glasses, and/or other means of display devices. In some embodiments, the display modules 202 are integrated with the control modules, for example, as a tablet device with a touchscreen. Further, the user 205 can both view data and input commands to the surgical robotic system 100 using the integrated display modules 202 and control modules.

The display modules 202 can display 3D images using a stereoscopic device, e.g., a visor or goggle. The 3D images provide an "endo view" (i.e., endoscopic view), which is a computer 3D model illustrating the anatomy of a patient. The "endo view" provides a virtual environment of the patient's interior and an expected location of an endoscope 118 inside the patient. A user 205 compares the "endo view" model to actual images captured by a camera to help mentally orient and confirm that the endoscope 118 is in the correct—or approximately correct—location within the patient. The "endo view" provides information about anatomical structures, e.g., the shape of an intestine or colon of the patient, around the distal end of the endoscope 118. The display modules 202 can simultaneously display the 3D model and computerized tomography (CT) scans of the anatomy the around distal end of the endoscope 118. Further, the display modules 202 may overlay pre-determined optimal navigation paths of the endoscope 118 on the 3D model and CT scans.

In some embodiments, a model of the endoscope 118 is displayed with the 3D models to help indicate a status of a surgical procedure. For example, the CT scans identify a lesion in the anatomy where a biopsy may be necessary. During operation, the display modules 202 may show a reference image captured by the endoscope 118 corresponding to the current location of the endoscope 118. The display modules 202 may automatically display different views of the model of the endoscope 118 depending on user settings and a particular surgical procedure. For example, the display modules 202 show an overhead fluoroscopic view of the endoscope 118 during a navigation step as the endoscope 118 approaches an operative region of a patient.

III. Instrument Device Manipulator

Figure 3:
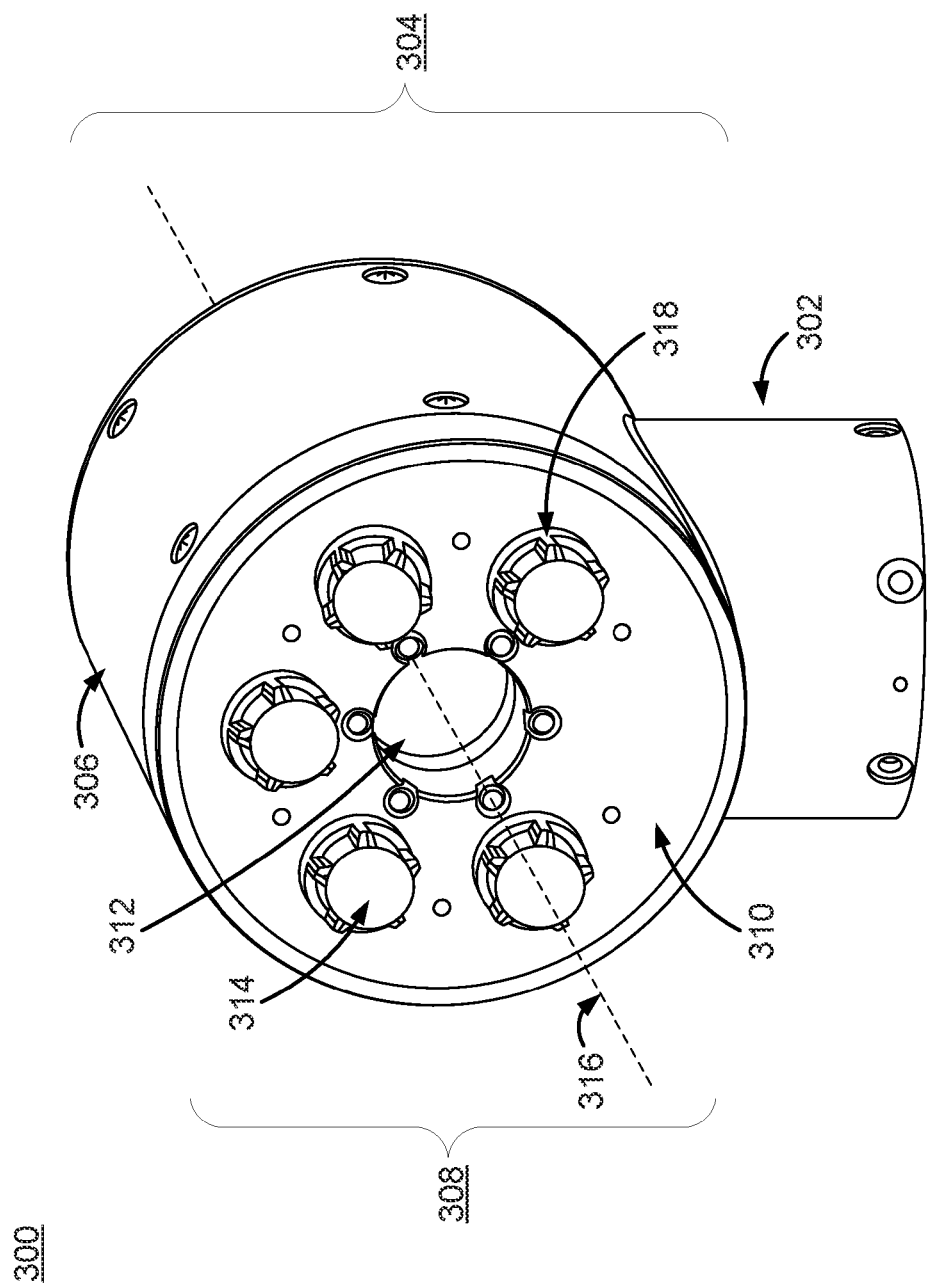
FIG. 3 illustrates a perspective view of an instrument device manipulator for a surgical robotic system, according to one embodiment.
Figure 4:
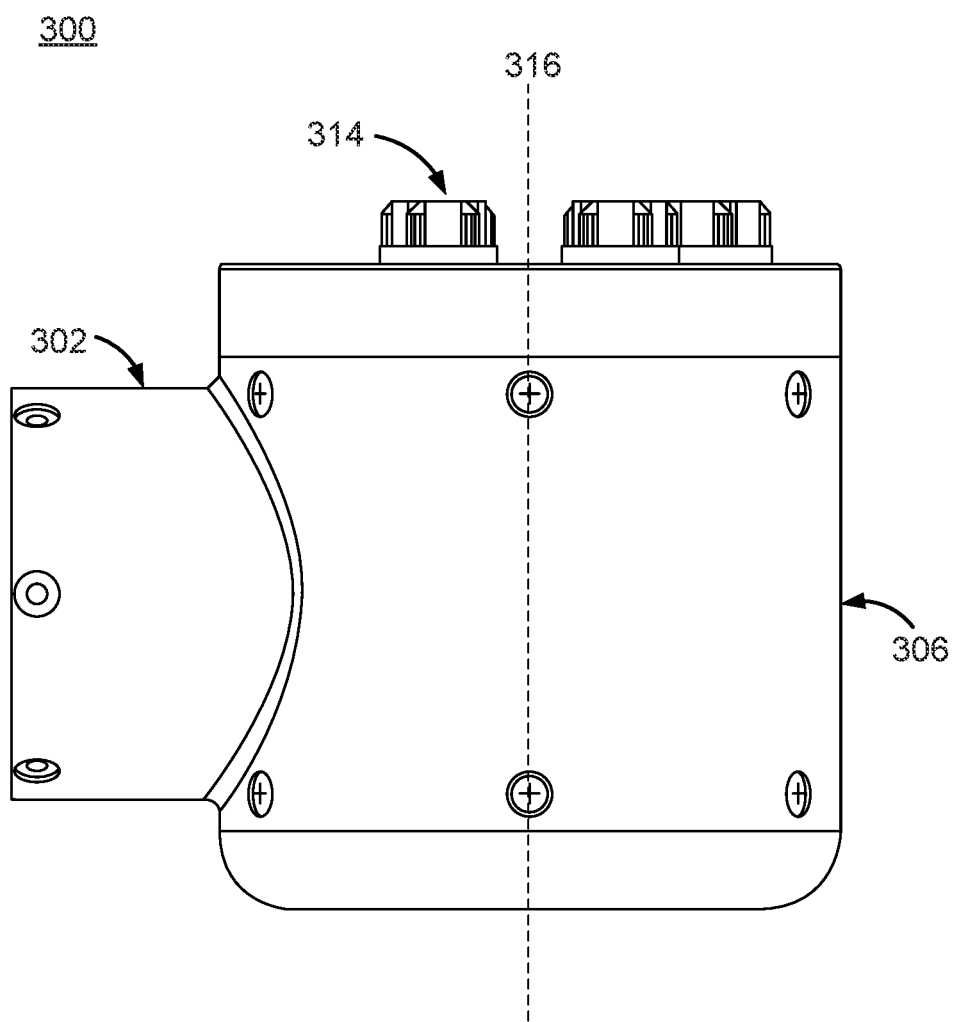
FIG. 4 illustrates a side view of the instrument device manipulator of FIG. 3, according to one embodiment.

FIG. 3 illustrates a perspective view of an instrument device manipulator (IDM) 300 for a surgical robotic system, and FIG. 4 is a side view of the IDM 300, according to one embodiment. The IDM 300 is configured to attach a surgical tool to a robotic surgical arm in a manner that allows the surgical tool to be continuously rotated or "rolled" about an axis of the surgical tool. The IDM 300 includes a base 302 and a surgical tool holder assembly 304. The surgical tool holder assembly 304 further includes an outer housing 306, a surgical tool holder 308, an attachment interface 310, a passage 312, and a plurality of torque couplers 314. The IDM 300 may be used with a variety of surgical tools (not shown in FIG. 3), which may include a housing and an elongated body, and which may be for a laparoscope, an endoscope, or other types of end-effectors of surgical instruments.

The base 302 removeably or fixedly mounts the IDM 300 to a surgical robotic arm of a surgical robotic system. In the embodiment of FIG. 3, the base 302 is fixedly attached to the outer housing 306 of the surgical tool holder assembly 304. In alternate embodiments, the base 302 may be structured to include a platform which is adapted to rotatably receive the surgical tool holder 308 on the face opposite from the attachment interface 310. The platform may include a passage aligned with the passage 312 to receive the elongated body of the surgical tool and, in some embodiments, an additional elongated body of a second surgical tool mounted coaxially with the first surgical tool.

The surgical tool holder assembly 304 is configured to secure a surgical tool to the IDM 300 and rotate the surgical tool relative to the base 302. Mechanical and electrical connections are provided from the surgical arm to the base 302 and then to the surgical tool holder assembly 304 to rotate the surgical tool holder 308 relative to the outer housing 306 and to manipulate and/or deliver power and/or signals from the surgical arm to the surgical tool holder 308 and ultimately to the surgical tool. Signals may include signals for pneumatic pressure, electrical power, electrical signals, and/or optical signals.

The outer housing 306 provides support for the surgical tool holder assembly 304 with respect to the base 302. The outer housing 306 is fixedly attached to the base 302 such that it remains stationary relative to the base 302, while allowing the surgical tool holder 308 to rotate freely relative to the outer housing 306. In the embodiment of FIG. 3, the outer housing 306 is cylindrical in shape and fully circumscribes the surgical tool holder 308. The outer housing 306 may be composed of rigid materials (e.g., metals or hard plastics). In alternate embodiments, the shape of the housing may vary.

The surgical tool holder 308 secures a surgical tool to the IDM 300 via the attachment interface 310. The surgical tool holder 308 is capable of rotating independent of the outer housing 306. The surgical tool holder 308 rotates about a rotational axis 316, which co-axially aligns with the elongated body of a surgical tool such that the surgical tool rotates with the surgical tool holder 308.

The attachment interface 310 is a face of the surgical tool holder 308 that attaches to the surgical tool. The attachment interface 310 includes a first portion of an attachment mechanism that reciprocally mates with a second portion of the attachment mechanism located on the surgical tool, which will be discussed in greater detail with regards to FIGS. 8A and 8B. The attachment interface 310 comprises a plurality of torque couplers 314 that protrude outwards from the attachment interface 310 and engage with respective instrument inputs on the surgical tool. In some embodiments, a surgical drape, coupled to a sterile adapter, may be used to create a sterile boundary between the IDM 300 and the surgical tool. In these embodiments, the sterile adapter may be positioned between the attachment interface 310 and the surgical tool when the surgical tool is secured to the IDM 300 such that the surgical drape separates the surgical tool and the patient from the IDM 300 and the surgical robotics system.

The passage 312 is configured to receive the elongated body of a surgical tool when the surgical tool is secured to the attachment interface 310. In the embodiment of FIG. 3, the passage 312 is co-axially aligned with the longitudinal axis of the elongated body of the surgical tool and the rotational axis 316 of the surgical tool holder 308. The passage 312 allows the elongated body of the surgical tool to freely rotate within the passage 312. This configuration allows the surgical tool to be continuously rotated or rolled about the rotational axis 316 in either direction with minimal or no restrictions.

The plurality of torque couplers 314 are configured to engage and drive the components of the surgical tool when the surgical tool is secured to the surgical tool holder 308. Each torque coupler 314 is inserted into a respective instrument input located on the surgical tool. The plurality of torque couplers 314 may also serve to maintain rotational alignment between the surgical tool and the surgical tool holder 308. As illustrated in FIG. 3, each torque coupler 314 is shaped as a cylindrical protrusion that protrudes outwards from the attachment interface 310. Notches 318 may be arranged along the outer surface area of the cylindrical protrusion. In some embodiments, the arrangement of the notches 318 creates a spline interface. The instrument inputs on the surgical tool are configured to have a complementary geometry to the torque couplers 314. For example, while not shown in FIG. 3, the instrument inputs of the surgical tool may be cylindrical in shape and have a plurality of ridges that reciprocally mate with the plurality of notches 318 on each torque coupler 314 and thus impart a torque on the notches 318. In alternate embodiments, the top face of the cylindrical protrusion may include the plurality of notches 318 configured to mate with a plurality of ridges in respective instrument inputs. In this configuration, each torque coupler 314 fully engages with its respective instrument input.

Additionally, each torque coupler 314 may be coupled to a spring that allows the torque coupler to translate. In the embodiment of FIG. 3, the spring causes each torque coupler 314 to be biased to spring outwards away from the attachment interface 310. The spring is configured to create translation in an axial direction, i.e., protract away from the attachment interface 310 and retract towards the surgical tool holder 308. In some embodiments, each torque coupler 314 is capable of partially retracting into the surgical tool holder 308. In other embodiments, each torque coupler 314 is capable of fully retracting into the surgical tool holder 308 such that the effective height of each torque coupler is zero relative to the attachment interface 310. In the embodiment of FIG. 3, the translation of each torque coupler 314 is actuated by an actuation mechanism, which will be described in further detail with regards to FIGS. 7-8. In various embodiments, each torque coupler 314 may be coupled to a single spring, a plurality of springs, or a respective spring for each torque coupler.

In addition, each torque coupler 314 is driven by a respective actuator that causes the torque coupler to rotate in either direction. Thus, once engaged with an instrument input, each torque coupler 314 is capable of transmitting power to tighten or loosen pull-wires within a surgical tool, thereby manipulating a surgical tool's end-effectors. In the embodiment of FIG. 3, the IDM 300 includes five torque couplers 314, but the number may vary in other embodiments depending on the desired number of degrees of freedom for a surgical tool's end-effectors. In some embodiments, a surgical drape, coupled to a sterile adapter, may be used to create a sterile boundary between the IDM 300 and the surgical tool. In these embodiments, the sterile adapter may be positioned between the attachment interface 310 and the surgical tool when the surgical tool is secured to the IDM 300, and the sterile adapter may be configured to transmit power from each torque coupler 314 to the respective instrument input.

The embodiment of the IDM 300 illustrated in FIG. 3 may be used in various configurations with a surgical robotic system. The desired configuration may depend on the type of surgical procedure being performed on a patient or the type of surgical tool being used during the surgical procedure. For example, the desired configuration of the IDM 300 may be different for an endoscopic procedure than for a laparoscopic procedure.

In a first configuration, the IDM 300 may be removeably or fixedly attached to a surgical arm such that the attachment interface 310 is proximal to a patient during the surgical procedure. In this configuration, hereinafter referred to as "front-mount configuration," the surgical tool is secured to the IDM 300 on a side proximal to the patient. A surgical tool for use with the front-mount configuration is structured such that the elongated body of the surgical tool extends from a side that is opposite of the attachment interface of the surgical tool. As a surgical tool is removed from the IDM 300 in a front-mount configuration, the surgical tool will be removed in a proximal direction to the patient.

In a second configuration, the IDM 300 may be removeably or fixedly attached to a surgical arm such that the attachment interface 310 is distal to a patient during the surgical procedure. In this configuration, hereinafter referred to as "back-mount configuration," the surgical tool is secured to the IDM 300 on a side distal to the patient. A surgical tool for use with the back-mount configuration is structured such that the elongated body of the surgical tool extends from the attachment interface of the surgical tool. This configuration increases patient safety during tool removal from the IDM 300. As a surgical tool is removed from the IDM 300 in a back-mount configuration, the surgical tool will be removed in a distal direction from the patient.

Certain configurations of a surgical tool may be structured such that the surgical tool can be used with an IDM in either a front-mount configuration or a back-mount configuration. In these configurations, the surgical tool includes an attachment interface on both ends of the surgical tool. For some surgical procedures, the physician may decide the configuration of the IDM depending on the type of surgical procedure being performed. For instance, the back-mount configuration may be beneficial for laparoscopic procedures wherein laparoscopic tools may be especially long relative to other surgical instruments. As a surgical arm moves about during a surgical procedure, such as when a physician directs a distal end of the surgical tool to a remote location of a patient (e.g., a lung or blood vessel), the increased length of laparoscopic tools causes the surgical arm to swing about a larger arc. Beneficially, the back-mount configuration decreases the effective tool length of the surgical tool by receiving a portion of the elongated body through the passage 312 and thereby decreases the arc of motion required by the surgical arm to position the surgical tool.

Figure 5:
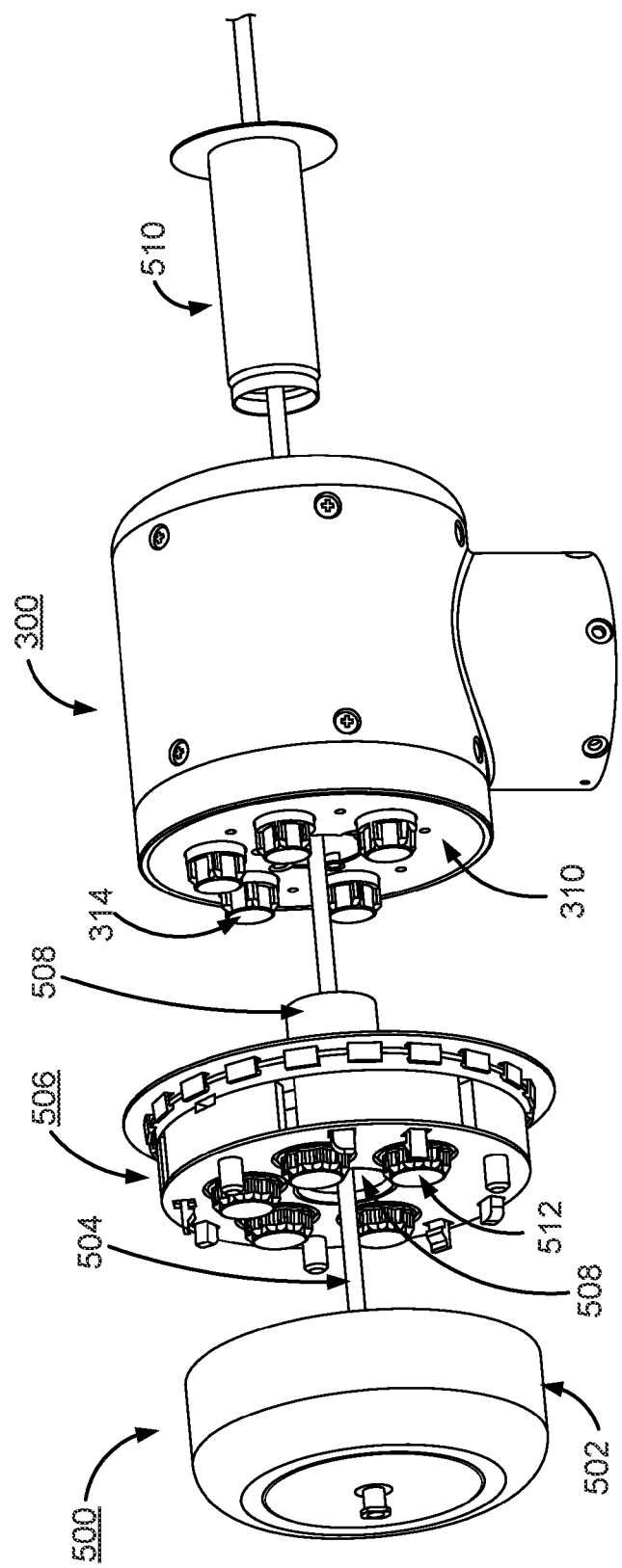
FIG. 5 illustrates a front-perspective exploded view of an example surgical tool secured to the instrument device manipulator of FIG. 3, according to one embodiment.
Figure 6:
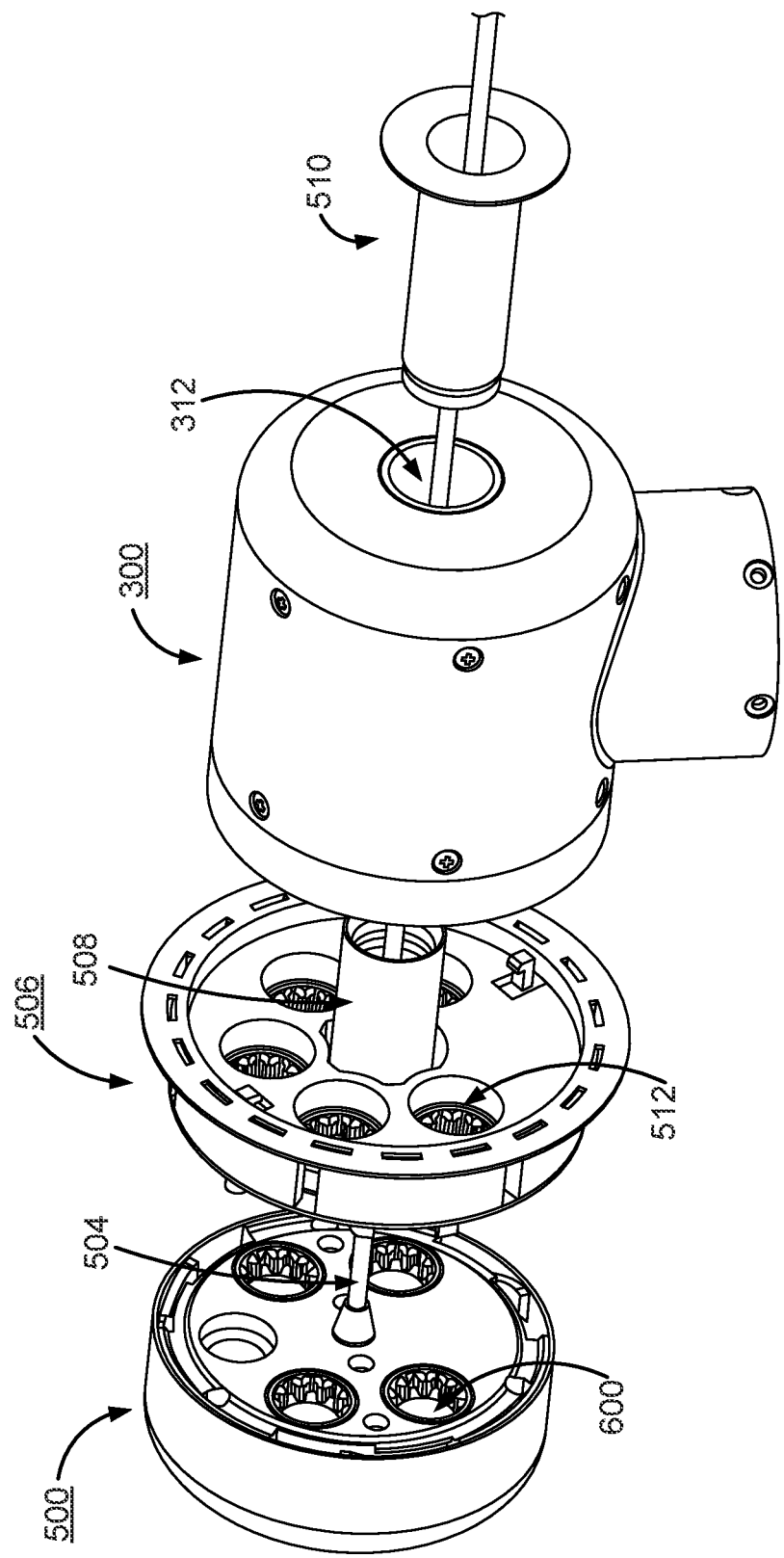
FIG. 6 illustrates a back-perspective exploded view of an example surgical tool secured to the instrument device manipulator of FIG. 3, according to one embodiment.

FIGS. 5-6 illustrate perspective exploded views of an example surgical tool 500 secured to the instrument device manipulator 300 of FIG. 3, according to one embodiment. The surgical tool 500 includes a housing 502, an elongated body 504, and a plurality of instrument inputs 600. As previously described, the elongated body 504 may be a laparoscope, an endoscope, or other surgical instrument having end-effectors. As illustrated, the plurality of torque couplers 314 protrude outwards from the attachment interface 310 to engage with the instrument inputs 600 of the surgical tool. The structure of the instrument inputs 600 can be seen in FIG. 6, wherein the instrument inputs 600 have corresponding geometry to the torque couplers 314 to ensure secure surgical tool engagement.

During a surgical procedure, a surgical drape may be used to maintain a sterile boundary between the IDM 300 and an outside environment (i.e., an operating room). In the embodiments of FIGS. 5-6, the surgical drape comprises a sterile adapter 506, a first protrusion 508, and a second protrusion 510. While not shown in FIGS. 5-6, a sterile sheet is connected to the sterile adapter and the second protrusion and drapes around the IDM 300 to create the sterile boundary.

The sterile adapter 506 is configured to create a sterile interface between the IDM 300 and the surgical tool 500 when secured to the IDM 300. In the embodiment of FIGS. 5-6, the sterile adapter 506 has a disk-like geometry that covers the attachment interface 310 of the IDM 300. The sterile adapter 506 comprises a central hole 508 that is configured to receive the elongated body 504 of the surgical tool 500. In this configuration, the sterile adapter 506 is positioned between the attachment interface 310 and the surgical tool 500 when the surgical tool 500 is secured to the IDM 300, creating the sterile boundary between the surgical tool 500 and the IDM 300 and allowing the elongated body 504 to pass through the passage 312. In certain embodiments, the sterile adapter 506 may be capable of rotating with the surgical tool holder 308, transmitting the rotational torque from the plurality of torque couplers 314 to the surgical tool 500, passing electrical signals between the IDM 300 and the surgical tool 500, or some combination thereof.

In the embodiment of FIGS. 5-6, the sterile adapter 506 further comprises a plurality of couplers 512. A first side of a coupler 512 is configured to engage with a respective torque coupler 314 while a second side of a coupler 512 is configured to engage with a respective instrument input 600. Similar to the structure of the plurality of torque couplers 314, each coupler 512 is structured as a cylindrical protrusion including a plurality of notches. Each side of the coupler 512 has complementary geometry to fully engage with the respective torque coupler 314 and the respective instrument input 600. Each coupler 512 is configured to rotate in a clockwise or counter-clockwise direction with the respective torque coupler 314. This configuration allows each coupler 512 to transfer rotational torque from the plurality of torque couplers 314 of the IDM 300 to the plurality of instrument inputs 600 of the surgical tool 500, and thus control the end-effectors of the surgical tool 500.

The first protrusion 508 and the second protrusion 510 are configured to pass through the passage 312 of the IDM 300 and mate with each other inside the passage 312. Each protrusion 508, 510 is structured to allow the elongated body 504 to pass through the protrusion and thus the passage 312. The connection of the first protrusion 508 and the second protrusion 510 creates the sterile boundary between the IDM 300 and the outside environment (i.e., an operating room). The surgical drape is discussed in further detail with regards to FIGS. 13-16.

IV. Surgical Tool Disengagement

FIG. 7 illustrates a zoomed-in, perspective view of an actuation mechanism for engagement and disengagement of a surgical tool 500 from a sterile adapter 506 of a surgical drape, according to one embodiment. Due to the configuration of the IDM 300 as described with regards to FIG. 3, the axis of surgical tool insertion into the patient during a surgical procedure is the same as the axis of surgical tool removal. To ensure patient safety during surgical tool removal, the surgical tool 500 can be de-articulated from the sterile adapter 506 and the IDM 300 before removing the surgical tool 500. In the embodiment of FIG. 7, the plurality of couplers 512 are configured to translate in an axial direction, i.e., protract away from and retract towards the sterile adapter 506. The translation of the plurality of couplers 512 is actuated by the actuation mechanism which ensures de-articulation of the surgical tool 500 by disengaging the plurality of couplers 512 from the respective instrument inputs 600. The actuation mechanism includes a wedge 702 and a pusher plate 704.

The wedge 702 is a structural component that activates the pusher plate 704 during the process of surgical tool disengagement. In the embodiment of FIG. 7, the wedge 702 is located within the housing 502 of the surgical tool 500 along the outer perimeter of the housing 502. As illustrated, the wedge 702 is oriented such that contact with the pusher plate 704 causes the pusher plate 704 to depress into the sterile adapter 506 if the housing 502 of the surgical tool 500 is rotated clockwise relative to the sterile adapter 506. In alternate embodiments, the wedge 702 may be configured such that the housing 502 of the surgical tool 500 is rotated counter-clockwise rather than clockwise. Geometries other than a wedge may be employed, such as an arch-shaped ramp, given that the structure is able to depress the pusher plate when rotating.

The pusher plate 704 is an actuator that disengages the plurality of couplers 512 from the surgical tool 500. Similar to the plurality of torque couplers 314, each of the couplers 512 may be coupled to one or more springs that bias each coupler 512 to spring outwards away from the sterile adapter 506. The plurality of couplers 512 are further configured to translate in an axial direction, i.e., protract away from and retract into the sterile adapter 506. The pusher plate 704 actuates the translational movement of the couplers 512. As the pusher plate 704 is depressed by the wedge 702, the pusher plate 704 causes the spring or plurality of springs coupled to each coupler 512 to compress, resulting in the couplers 512 retracting into the sterile adapter 506. In the embodiment of FIG. 7, the pusher plate 704 is configured to cause simultaneous retraction of the plurality of couplers 512. Alternate embodiments may retract the couplers 512 in a specific sequence or a random order. In the embodiment of FIG. 7, the pusher plate 704 causes the plurality of couplers 512 to partially retract into the sterile adapter 506. This configuration allows a surgical tool 500 to be de-articulated from the sterile adapter 506 before the surgical tool 500 is removed. This configuration also allows a user to de-articulate the surgical tool 500 from the sterile adapter 506 at any desired time without removing the surgical tool 500. Alternate embodiments may fully retract the plurality of couplers 512 into the sterile adapter 506 such that the effective height of each coupler 512 measured is zero. In some embodiments, the pusher plate 704 may cause the plurality of torque couplers 314 to retract synchronously with the plurality of respective couplers 512.

FIGS. 8A and 8B illustrate a process of engaging and disengaging a surgical tool from a sterile adapter, according to one embodiment. FIG. 8A illustrates a sterile adapter 506 and a surgical tool 500 in a secured position, such that the two components are secured together and the plurality of couplers 512 are fully engaged with respective instrument inputs 600 of the surgical tool 500. To achieve the secured position as illustrated in FIG. 8A, the elongated body 504 (not shown) of the surgical tool 500 is passed through the central hole 508 (not shown) of the sterile adapter 506 until mating surfaces of the surgical tool 500 and the sterile adapter 506 are in contact, and the surgical tool 500 and the sterile adapter 506 are secured to each other by a latching mechanism. In the embodiments of FIGS. 8A and 8B, the latching mechanism comprises a ledge 802 and a latch 804.

The ledge 802 is a structural component that secures the latch 804 in the secured position. In the embodiment of FIG. 8A, the ledge 802 is located within the housing 502 of the surgical tool 500 along the outer perimeter of the housing 502. As illustrated in FIG. 8A, the ledge 802 is oriented such that it rests below a protrusion on the latch 804, preventing the latch 804 and thereby the sterile adapter 506 from pulling away from the surgical tool 500 due to the sprung-up nature of the plurality of couplers 512, as described with regards to FIG. 7.

The latch 804 is a structural component that mates with the ledge 802 in the secured position. In the embodiment of FIG. 8A, the latch 804 protrudes from the mating surface of the sterile adapter 506. The latch 804 comprises a protrusion that is configured to rest against the ledge 802 when the surgical tool 500 is secured to sterile adapter 506. In the embodiment of FIG. 8A, the housing 502 of the surgical tool 500 is capable of rotating independent of the rest of the surgical tool 500. This configuration allows the housing 502 to rotate relative to the sterile adapter 506 such that the ledge 802 is secured against the latch 804, thereby securing the surgical tool 500 to the sterile adapter 502. In the embodiment of FIG. 8A, the housing 502 is rotated counter-clockwise to achieve the secured position, but other embodiments may be configured for clockwise rotation. In alternate embodiments, the ledge 802 and the latch 804 may have various geometries that lock the sterile adapter 506 and the surgical tool 500 in the secured position.

FIG. 8B illustrates the sterile adapter 506 and the surgical tool 500 in an unsecured position, in which the surgical tool 500 may be removed from the sterile adapter 506. As previously described, the housing 502 of the surgical tool 500 is capable of rotating independent of the rest of the surgical tool 500. This configuration allows the housing 502 to rotate even while the plurality of couplers 512 are engaged with the instrument inputs 600 of the surgical tool 500. To transition from the secured position to the unsecured position, a user rotates the housing 502 of the surgical tool 500 clockwise relative to the sterile adapter 506. During this rotation, the wedge 702 contacts the pusher plate 704 and progressively depresses the pusher plate 704 as it slides against the angled plane of the wedge 702, thereby causing the plurality of couplers 512 to retract into the sterile adapter 506 and disengage from the plurality of instrument inputs 600. Further rotation causes the latch 804 to contact an axial cam 806, which is structured similar to wedge 702. As the latch 804 contacts the axial cam 806 during rotation, the axial cam 806 causes the latch 804 to flex outwards away from the surgical tool 500 such that the latch 804 is displaced from the ledge 802. In this unsecured position, the plurality of couplers 512 are retracted, and the surgical tool 500 can be removed from the sterile adapter 506, in the embodiment of FIG. 8B. In other embodiments, the axial cam 806 may have various geometries such that rotation causes the latch 804 to flex outwards.

In alternate embodiments, the direction of rotation of the housing 502 of the surgical tool 500 may be configured as counter-clockwise rotation to unsecure the latch 804 from the ledge 802. Additionally, alternate embodiments may include similar components but the location of the components may be switched between the sterile adapter 506 and the surgical tool 500. For example, the ledge 802 may be located on the sterile adapter 506 while the latch 804 may be located on the surgical tool 500. In other embodiments, an outer portion of the sterile adapter 506 may be rotatable relative to the plurality of couplers 512 rather than the housing 502 of the surgical tool 500. Alternate embodiments may also include a feature to lock the rotation of the housing 502 of the surgical tool 502 when the housing 502 is fully rotated relative to the instrument inputs 600. This configuration prevents rotation of the surgical tool if the instrument inputs 600 have been de-articulated from the couplers 512. In some embodiments, the retraction and protraction of the couplers 512 may be coupled with a respective retraction and protraction of the torque couplers 314, such that a coupler 512 engaged with a torque coupler 314 will translate together.

Figure 9A:
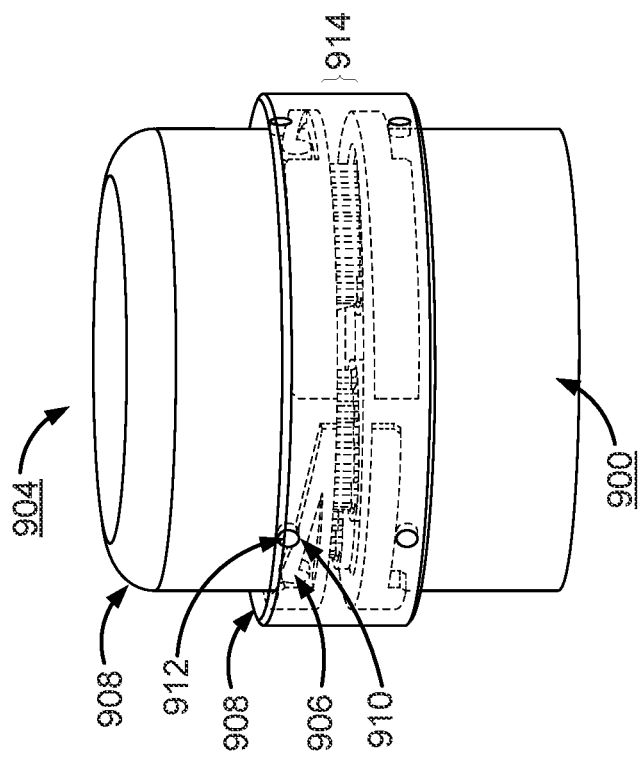
FIGS. 9A and 9B illustrate a process of engaging and disengaging a surgical tool from a sterile adapter, according to an additional embodiment.
Figure 9B:
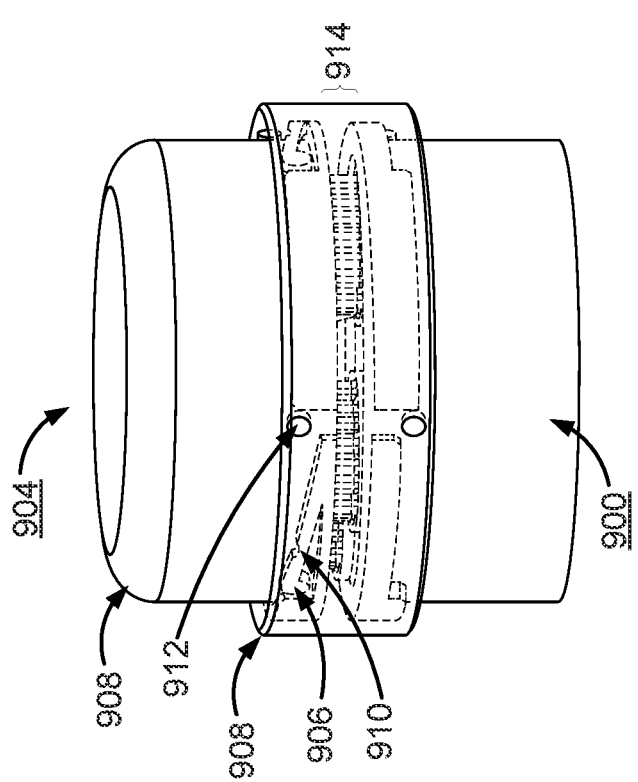

FIGS. 9A and 9B illustrate a process of surgical tool engagement and disengagement of a surgical tool from a sterile adapter, according to another embodiment. In the embodiment of FIGS. 9A and 9B, a sterile adapter 900 may include an outer band 902 that secures the surgical tool 904 to the sterile adapter 900. As illustrated in FIGS. 9A and 9B, the surgical tool 902 comprises a ramp 906 on the outer surface of the housing 908. The ramp 906 includes a notch 910 that is configured to receive a circular protrusion 912, which is positioned on an inner surface of the outer band 902 of the sterile adapter 900. The outer band 902 is capable of rotating independent of and relative to the sterile adapter 900 and the surgical tool 904. As the outer band 902 rotates in a first direction, the circular protrusion 912 glides up the surface of the ramp 906 until the circular protrusion 912 is nested within the notch 910, thereby securing the sterile adapter 900 and the surgical tool 904 together. Rotation of the outer band 902 in a second direction causes the sterile adapter 900 and the surgical tool 904 to unsecure from each other. In certain embodiments, this mechanism may be coupled with a de-articulation of the plurality of couplers 914 on the sterile adapter 900, as described with regards to FIGS. 7-8.

Alternate embodiments of surgical tool disengagement may include additional features, such as an impedance mode. With an impedance mode, the surgical robotics system may control whether the surgical tool can be removed from the sterile adapter by a user. The user may initiate the disengagement mechanism by rotating the outer housing of the surgical tool and unsecuring the surgical tool from the sterile adapter, but the surgical robotics system may not release the couplers from the instrument inputs. Only once the surgical robotics system has transitioned into the impedance mode are the couplers released and the user can remove the surgical tool. An advantage of keeping the surgical tool engaged is that the surgical robotics system can control the end-effectors of the surgical tool and position them for tool removal before the surgical tool is removed to minimize damage to the surgical tool. To activate an impedance mode, the pusher plate 704 may have a hard-stop such that the pusher plate can be depressed up to a certain distance. In some embodiments, the hard-stop of the pusher plate may be adjustable such that the hard-stop coincides with the maximum amount of rotation of the housing of the surgical tool. Thus, once the full rotation is reached, the hard-stop is also met by the pusher plate. A plurality of sensors may detect these events and trigger the impedance mode.

Certain situations may require emergency tool removal during a surgical procedure in which the impedance mode may not be desirable. In some embodiments, the hard-stop of the pusher plate may have compliance, such that the hard-stop may yield in an emergency situation. The hard-stop of the pusher plate may be coupled to a spring, allowing the hard-stop to yield in response to additional force. In other embodiments, the hard-stop of the pusher plate may be rigid such that emergency tool removal occurs by removing the latch that secures the surgical tool to the sterile adapter.

V. Roll Mechanism

Figure 10A:
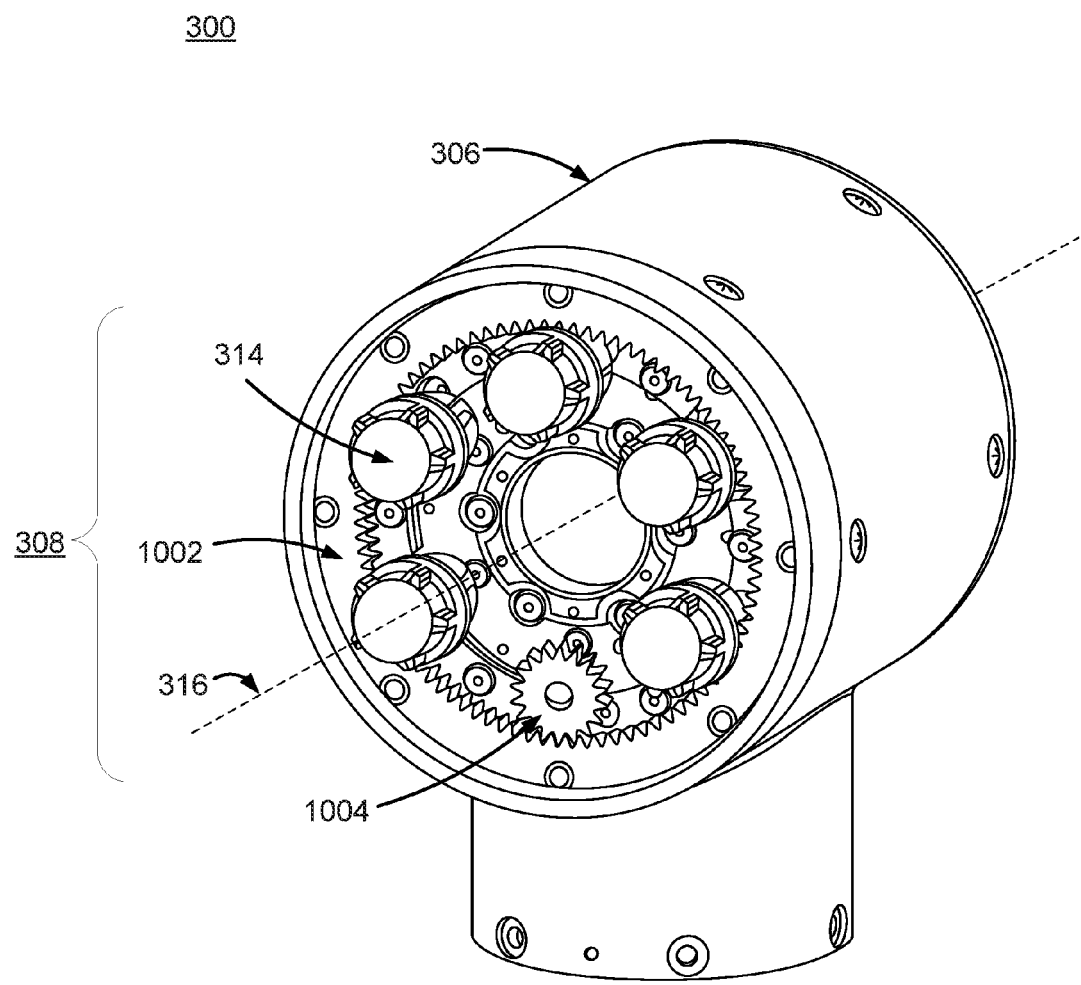
FIG. 10A illustrates a perspective view of a mechanism for rolling a surgical tool holder within an instrument device manipulator, according to one embodiment.

FIG. 10A illustrates a perspective view of a mechanism for rolling a surgical tool holder 308 within an instrument device manipulator 300, according to one embodiment. As illustrated in FIG. 10A, the attachment interface 310 is removed to expose the roll mechanism. This mechanism allows the surgical tool holder 308 to continuously rotate or "roll" about the rotational axis 316 in either direction. The roll mechanism comprises a stator gear 1002 and a rotor gear 1004.

The stator gear 1002 is a stationary gear configured to mate with the rotor gear 1004. In the embodiment of FIG. 10A, the stator gear 1002 is a ring-shaped gear comprising gear teeth along the inner circumference of the ring. The stator gear 1002 is fixedly attached to the outer housing 306 behind the attachment interface 310. The stator gear 1002 has the same pitch as the rotor gear 1004, such that the gear teeth of the stator gear 1002 are configured to mate with the gear teeth of the rotor gear 1004. The stator gear 1002 may be composed of rigid materials (e.g., metals or hard plastics).

The rotor gear 1004 is a rotating gear configured to induce rotation of the surgical tool holder 308. As illustrated in FIG. 10A, the rotor gear 1004 is a circular gear comprising gear teeth along its outer circumference. The rotor gear 1004 is positioned behind the attachment interface 310 and within the inner circumference of the stator gear 1002 such that the gear teeth of the rotor gear 1004 mate with the gear teeth of the stator gear. As previously described, the rotor gear 1004 and the stator gear 1002 have the same pitch. In the embodiment of FIG. 10A, the rotor gear 1004 is coupled to a drive mechanism (e.g., a motor) that causes the rotor gear 1004 to rotate in a clockwise or counter-clockwise direction. The drive mechanism may receive signals from an integrated controller within the surgical tool holder assembly 304. As the drive mechanism causes the rotor gear 1004 to rotate, the rotor gear 1004 travels along the gear teeth of the stator gear 1002, thereby causing the surgical tool holder 308 to rotate. In this configuration, the rotor gear 1004 is capable of continuously rotating in either direction and thus allows the surgical tool holder 308 to achieve infinite roll about the rotational axis 316. Alternate embodiments may use similar mechanisms to allow for infinite roll, such as a configuration of a ring gear and a pinion gear.

Figure 10B:
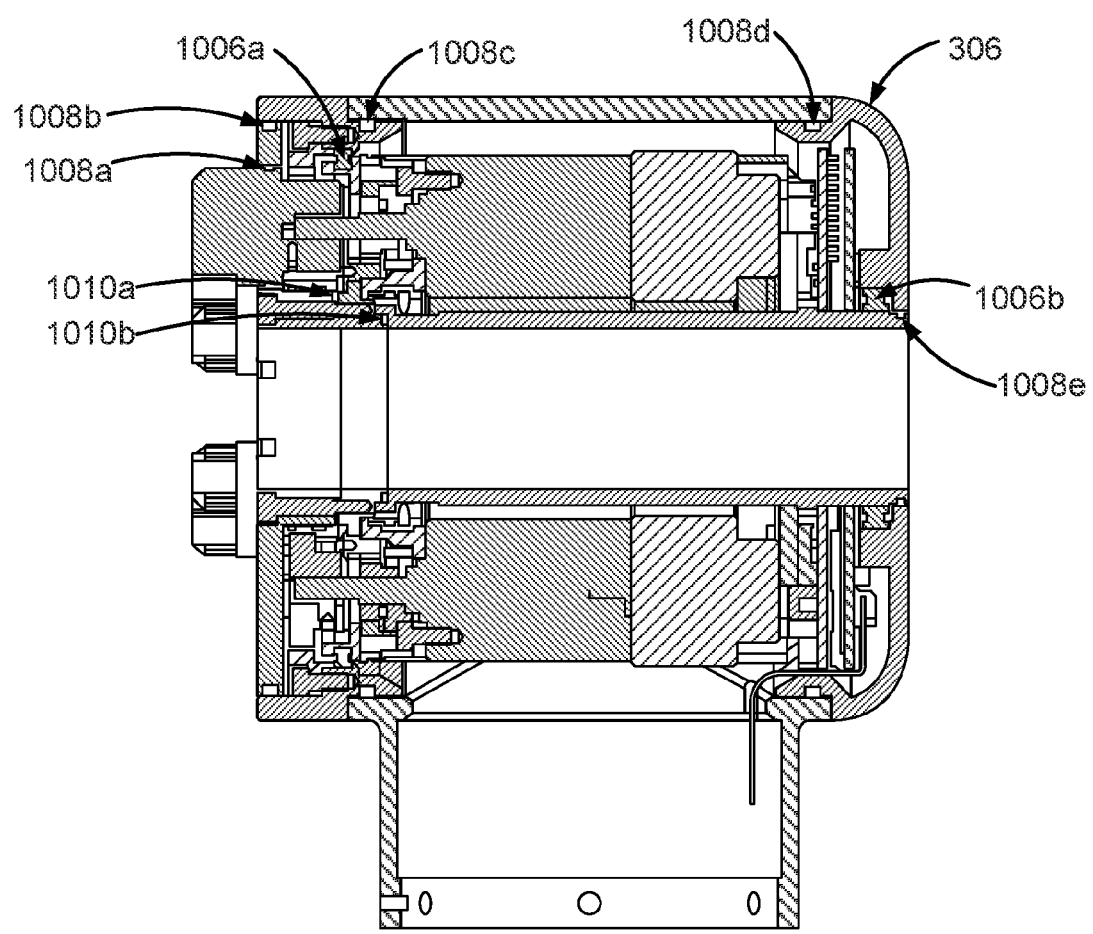
FIG. 10B illustrates a cross-sectional view of an instrument device manipulator, according to one embodiment.

FIG. 10B illustrates a cross-sectional view of an instrument device manipulator 300, according to one embodiment. As illustrated in FIB. 10B, the roll mechanism is coupled with a plurality of bearing 1006. A bearing is a mechanical component that reduces friction between moving parts and facilitates rotation around a fixed axis. One bearing alone is capable of supporting the radial or torsional loading as the surgical tool holder 308 rotates within the outer housing 306. In the embodiment of FIG. 10B, the IDM 300 includes two bearings 1006a, 1006b fixedly attached to the surgical tool holder 308 such that a plurality of components (such as balls or cylinders) within the bearings 1006 contacts the outer housing 306. A first bearing 1006a is secured at a first end behind the attachment interface 310 and a second bearing 1006b is secured at a second end. This configuration improves rigidity and support between the first end and the second end of the surgical tool holder 308 as the surgical tool holder 308 rotates within the outer housing 306. Alternate embodiments may include additional bearings that provide additional support along the length of the surgical tool holder.

FIG. 10B also illustrates sealing components within the IDM 300, according to one embodiment. The IDM 300 comprises a plurality of O-rings 1008 and a plurality of gaskets 1010 which are configured to seal a junction between two surfaces to prevent fluids from entering the junction. In the embodiment of FIG. 10B, the IDM includes O-rings 1008a, 1008b, 1008c, 1008d, 1008e between junctions of the outer housing and gaskets 1010a, 1010b between junctions within the surgical tool holder 308. This configuration helps to maintain sterility of the components within the IDM 300 during a surgical procedure. Gaskets and O-rings are typically composed of strong elastomeric materials (e.g., rubber).

VI. Electrical Componentry

Figure 11A:
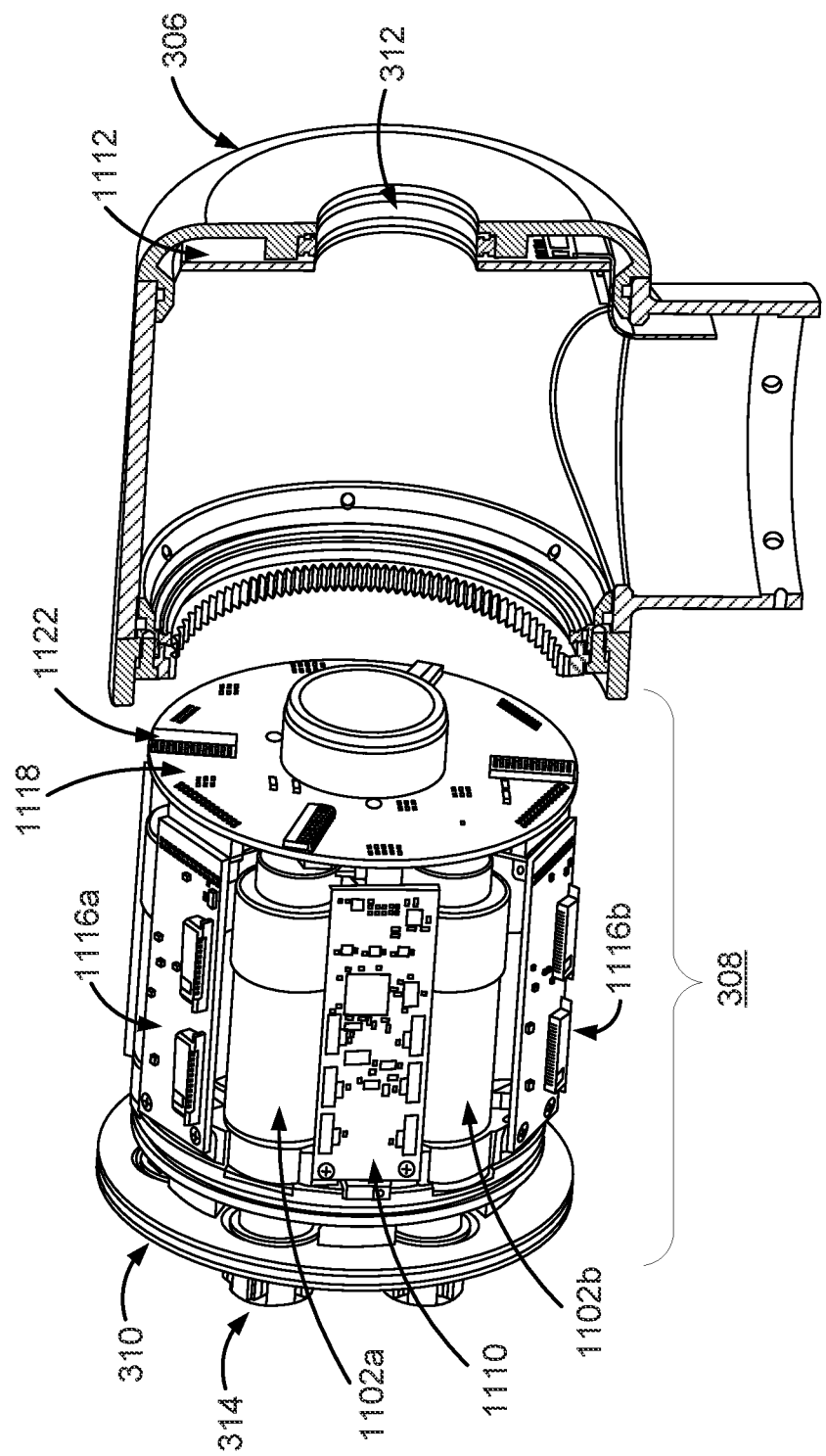
FIGS. 11A and 11B illustrate partially exploded, perspective views of the internal components of an instrument device manipulator and certain electrical components thereof, according to one embodiment.

FIG. 11A illustrates a partially exploded, perspective view of the internal components of an instrument device manipulator and certain electrical components thereof, according to one embodiment. The internal components of the surgical tool holder 308 include a plurality of actuators 1102, a motor, a gearhead (not shown), a torque sensor (not shown), a torque sensor amplifier 1110, a slip ring 1112, a plurality of encoder boards 1114, a plurality of motor power boards 1116, and an integrated controller 1118.

The plurality of actuators 1102 drive the rotation of each of the plurality of torque couplers 314. In the embodiment of FIG. 11A, an actuator, such as 1102a or 1102b, is coupled to a torque coupler 314 via a motor shaft. The motor shaft may be a keyed shaft such that it includes a plurality of grooves to allow the motor shaft to securely mate to a torque coupler 314. The actuator 1102 causes the motor shaft to rotate in a clockwise or counter-clockwise direction, thereby causing the respective torque coupler 314 to rotate in that direction. In some embodiments, the motor shaft may be torsionally rigid but spring compliant, allowing the motor shaft and thus the torque coupler 314 to rotate and to translate in an axial direction. This configuration may allow the plurality of torque couplers 314 to retract and protract within the surgical tool holder 308. Each actuator 1102 may receive electrical signals from the integrated controller 1118 indicating the direction and amount to rotate the motor shaft. In the embodiment of FIG. 11A, the surgical tool holder 308 includes five torque couplers 314 and thus five actuators 1102.

The motor drives the rotation of the surgical tool holder 308 within the outer housing 306. The motor may be structurally equivalent to one of the actuators, except that it is coupled to the rotor gear 1004 and stator gear 1002 (see FIG. 10A) for rotating the surgical tool holder 308 relative to the outer housing 306. The motor causes the rotor gear 1004 to rotate in a clockwise or counter-clockwise direction, thereby causing the rotor gear 1004 to travel about the gear teeth of the stator gear 1002. This configuration allows the surgical tool holder 308 to continuously roll or rotate without being hindered by potential wind-up of cables or pull-wires. The motor may receive electrical signals from the integrated controller 1118 indicating the direction and amount to rotate the motor shaft.

The gearhead controls the amount of torque delivered to the surgical tool 500. For example, the gearhead may increase the amount of torque delivered to the instrument inputs 600 of the surgical tool 500. Alternate embodiments may be configured such that the gearhead decreases the amount of torque delivered to the instrument inputs 600.

The torque sensor measures the amount of torque produced on the rotating surgical tool holder 308. In the embodiment shown in FIG. 11A, the torque sensor is capable of measuring torque in the clockwise and the counter-clockwise direction. The torque measurements may be used to maintain a specific amount of tension in a plurality of pull-wires of a surgical tool. For instance, some embodiments of the surgical robotics system may have an auto-tensioning feature, wherein, upon powering on the surgical robotics system or engaging a surgical tool with an IDM, the tension on the pull-wires of the surgical tool will be pre-loaded. The amount of tension on each pull-wire may reach a threshold amount such that the pull-wires are tensioned just enough to be taut. The torque sensor amplifier 1110 comprises circuitry for amplifying the signal that measures the amount of torque produced on the rotating surgical tool holder 308. In some embodiments, the torque sensor is mounted to the motor.

The slip ring 1112 enables the transfer of electrical power and signals from a stationary structure to a rotating structure. In the embodiment of FIG. 11A, the slip ring 1112 is structured as a ring including a central hole that is configured to align with the passage 312 of the surgical tool holder 308, as is also shown in an additional perspective view of the slip ring 1112 in FIG. 11B. A first side of the slip ring 1112 includes a plurality of concentric grooves 1120 while a second side of the slip ring 1112 includes a plurality of electrical components for the electrical connections provided from the surgical arm and the base 302, as described with regards to FIG. 3. The slip ring 1112 is secured to the outer housing 306 of the surgical tool holder 308 at a specific distance from the outer housing 306 to allocate space for these electrical connections. The plurality of concentric grooves 1120 are configured to mate with a plurality of brushes 1122 attached to the integrated controller. The contact between the grooves 1120 and the brushes 1122 enables the transfer of electrical power and signals from the surgical arm and base to the surgical tool holder.

The plurality of encoder boards 1114 read and process the signals received through the slip ring from the surgical robotic system. Signals received from the surgical robotic system may include signals indicating the amount and direction of rotation of the surgical tool, signals indicating the amount and direction of rotation of the surgical tool's end-effectors and/or wrist, signals operating a light source on the surgical tool, signals operating a video or imaging device on the surgical tool, and other signals operating various functionalities of the surgical tool. The configuration of the encoder boards 1114 allows the entire signal processing to be performed completely in the surgical tool holder 308. The plurality of motor power boards 1116 each comprises circuitry for providing power to the motors.

The integrated controller 1118 is the computing device within the surgical tool holder 308. In the embodiment of FIG. 11A, the integrated controller 1118 is structured as a ring including a central hole that is configured to align with the passage 312 of the surgical tool holder 308. The integrated controller 1118 includes a plurality of brushes 1122 on a first side of the integrated controller 1118. The brushes 1122 contact the slip ring 1112 and receive signals that are delivered from the surgical robotics system through the surgical arm, the base 302, and finally through the slip ring 1112 to the integrated controller 1118. As a result of the received signals, the integrated controller 1118 is configured to send various signals to respective components within the surgical tool holder 308. In some embodiments, the functions of the encoder boards 1114 and the integrated controller 1118 may be distributed in a different manner than is described here, such that the encoder boards 1114 and the integrated controller 1118 may perform the same functions or some combination thereof.

Figure 11B:
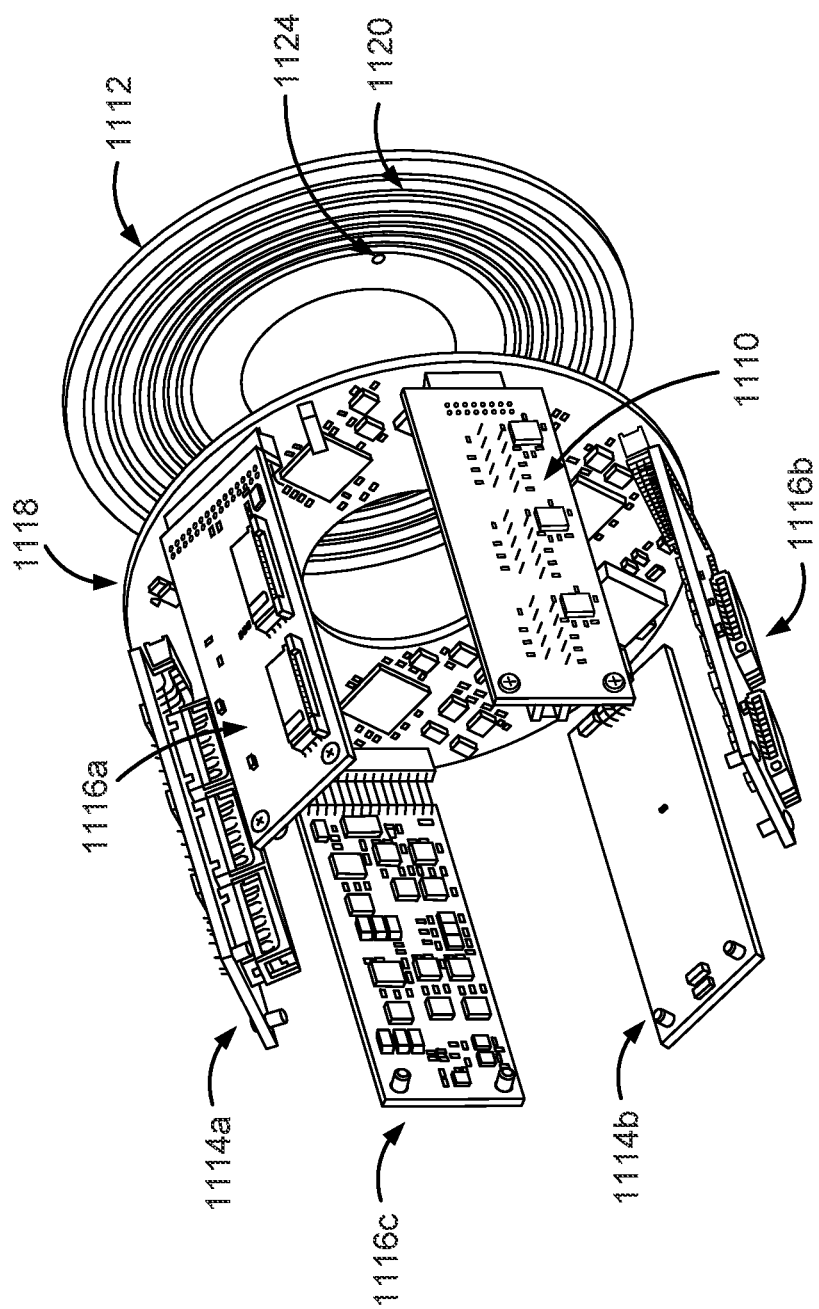

FIG. 11B illustrates a partially exploded, perspective view of the internal components of an instrument device manipulator and certain electrical components thereof, according to one embodiment. The embodiment of FIG. 11B includes two encoder boards 1114a and 1114b, a torque sensor amplifier 1110, and three motor power boards 1116a, 1116b, and 1116c. These components are secured to the integrated controller 1118 and protrude outwards, extending perpendicularly from the integrated controller 1118. This configuration provides room for the plurality of actuators 1102 and motor to be positioned within the electrical boards.

As discussed with regards to FIG. 11A, the slip ring 1112 is secured at a specific distance from the outer housing 306. To ensure correct space allocation between the slip ring 1112 and the outer housing 306 for the electrical connections from the surgical arm and base 302 to the slip ring 1112, in the embodiment of FIG. 11B, the slip ring 1112 is supported by a plurality of alignment pins, a plurality of coil springs, and a shim. The slip ring 1112 includes a hole 1124 on each side of the center hole of the slip ring 1112 that is configured to accept a first side of an alignment pin while a second side of the alignment pin is inserted into a respective hole in the outer housing 306. The alignment pins may be composed of rigid materials (e.g., metal or hard plastics). The plurality of coil springs are secured around the center of the slip ring 1112 and configured to bridge the space and maintain contact between the slip ring 1112 and the outer housing 306. The coil springs may beneficially absorb any impact to the IDM 300. The shim is ring-shaped spacer that is positioned around the center hole of the slip ring 1112 to add further support between the slip ring 1112 and the outer housing 306. In addition, these components provide stability to the slip ring 1112 as the plurality of brushes 1122 on the integrated controller 1118 contact and rotate against the plurality of concentric grooves 1120. In alternate embodiments, the number of alignment pins, coil springs, and shims may vary until the desired support between the slip ring 1112 and the outer housing 306 is achieved.

FIG. 12 illustrates a zoomed-in, perspective view of electrical components of an instrument device manipulator 300 for roll indexing the surgical tool holder 308, according to one embodiment. Roll indexing monitors the position of the surgical tool holder 308 relative to the outer housing 306 such that the position and orientation of the surgical tool 500 is continuously known by the surgical robotics system. The embodiment of FIG. 12 includes a micro switch 1202 and a boss 1204. The micro switch 1202 and the boss 1204 are secured within the surgical tool holder 308. The boss 1204 is a structure on the outer housing 306 that is configured to contact the micro switch 1202 as the surgical tool holder 308 rotates, thus activating the micro switch each time there is contact with the boss 1204. In the embodiment of FIG. 12, there is one boss 1204 that serves as a single reference point for the micro switch 1202.

VII. Surgical Drape

Figure 13:
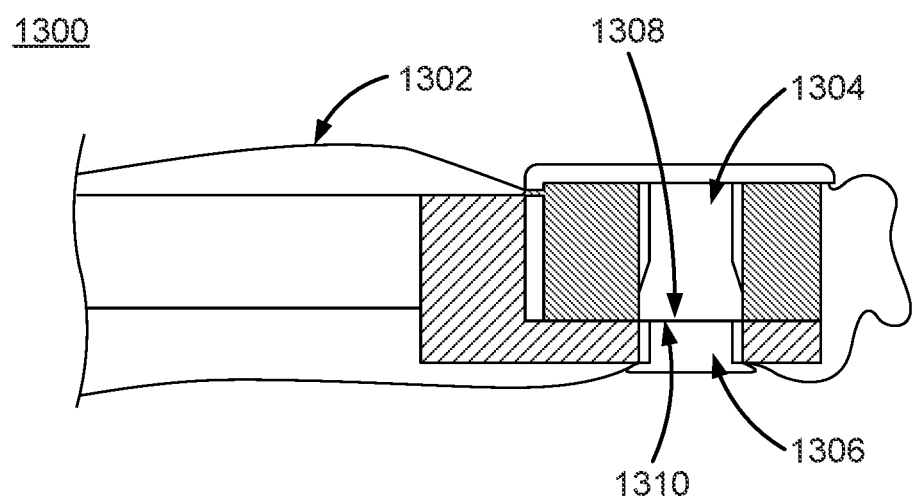
FIG. 13 illustrates a cross-sectional view of a surgical drape for an instrument device manipulator for a surgical robotics system, according to one embodiment.

FIG. 13 illustrates a cross-sectional view of a surgical drape for an instrument device manipulator for a surgical robotics system, according to one embodiment. The surgical drape 1300 provides a sterile boundary for the IDM, the surgical arm, and other portions of the surgical robotics system during a surgical procedure. In the embodiment of FIG. 13, the surgical drape 1300 is configured for use with an IDM that includes a passage configured to receive an elongated body of a surgical tool when the surgical tool is attached to the IDM, such as IDM 300. The surgical drape 1300 comprises a sterile sheet 1302, a first protrusion 1304, and a second protrusion 1306.

The sterile sheet 1302 creates and maintains a sterile environment for portions of the surgical robotics system during a surgical procedure. In the embodiment of FIG. 13, the sterile sheet 1302 is configured to cover the IDM 300, the surgical arm, and portions of the surgical robotics system. The sterile sheet 1302 may be composed of a variety of materials, such as plastics (e.g., polypropylene), paper, and other materials that may be resistant to fluids.

The first protrusion 1304 is a cylindrical tube configured to receive an elongated body of a surgical tool, such as elongated body 504 of surgical tool 500. In the embodiment of FIG. 13, the first protrusion 1304 is connected to a first portion of the sterile sheet 1302, and a first end of the first protrusion 1304 is configured to be inserted into a first end of the passage 312. The first end of the first protrusion 1304 includes a mating interface 1308 that is configured to mate with a reciprocal mating interface 1310 on the second protrusion 1306. The first protrusion 1304 may be composed of rigid materials (e.g., metals or hard plastics).

The second protrusion 1306 is a cylindrical tube configured to receive an elongated body of a surgical tool, such as elongated body 504 of surgical tool 500. In the embodiment of FIG. 13, the second protrusion 1306 is connected to a second portion of the sterile sheet 1302, and a first end of the second protrusion 1306 is configured to be inserted into a second end of the passage 312, such that the first protrusion 1304 and the second protrusion 1306 are inserted into opposite ends of the passage 312. The first end of the second protrusion 1306 includes a reciprocal mating interface 1310 that is configured to removeably couple with the mating interface 1308 on the first protrusion 1304 inside the passage 312. When coupled to each other, the mating interface 1308 and the reciprocal mating interface 1310 create a sterile junction. The second protrusion 1306 may be composed of rigid materials (e.g., metals or hard plastics). In alternate embodiments, coupling mechanisms may include hook-and-loop fasteners, friction-fit tubes, threaded tubes, and other suitable coupling mechanisms.

Figure 14:
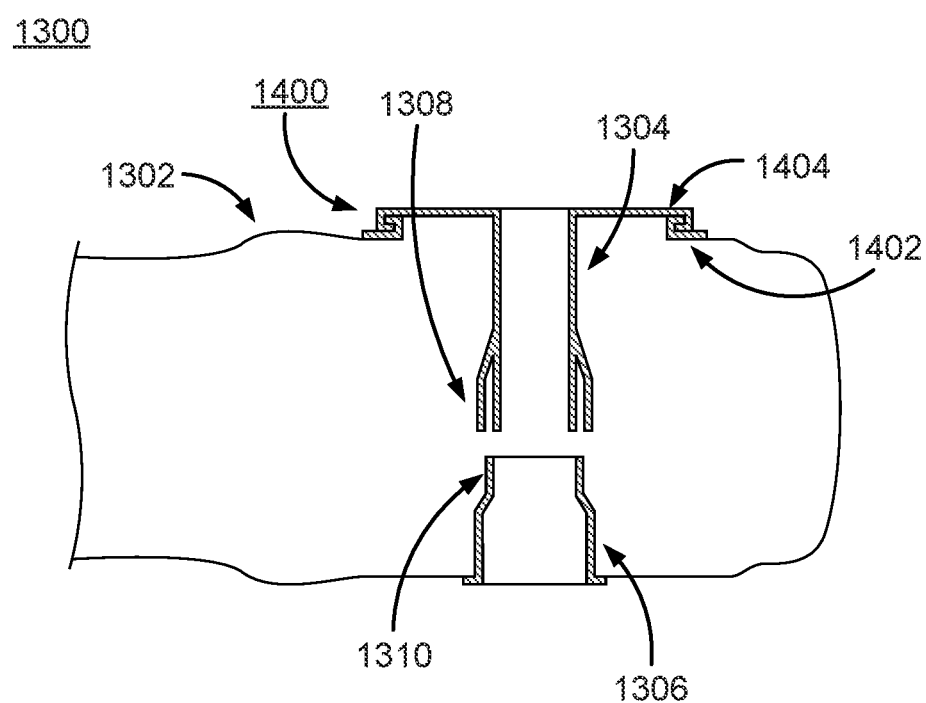
FIG. 14 illustrates a cross-sectional view of reciprocal mating interfaces of a surgical drape for a surgical tool holder, according to one embodiment.

FIG. 14 illustrates a cross-sectional view of reciprocal mating interfaces of a surgical drape for a surgical tool holder, according to one embodiment. As described with regards to FIG. 13, the first end of the first protrusion 1304 includes a mating interface 1308. The mating interface 1308 is structured as two concentric tubes with a crevice between the concentric tubes, as shown by the cross-section in FIG. 14, wherein the crevice is a ring configured to receive an end of another tube. In the embodiment of FIG. 14, the reciprocal mating interface 1310 at the first end of the second protrusion 1306 is structured as a tube that tapers such that the diameter at the first end of the tube is smaller relative to the rest of the tube. The tapered end facilitates easy insertion of the reciprocal mating interface 1310 into the mating interface 1308. In addition, it is possible for the inner surfaces of the first protrusion 1304 and the second protrusion 1306 to contact an unsterile surface while the outer surfaces are able to remain sterile. The junction between the mating interface 1308 and the reciprocal mating interface 1310 when secured to each other creates a convoluted path by enveloping the first end of the second protrusion 1306 into the crevice. This configuration ensures that any surfaces of the first protrusion 1304 or the second protrusion 1306 that contacted an unsterile surface are enveloped within the junction. This configuration further ensures that any fluids may not be able to travel across the junction between the inner surfaces and the outer surfaces and that a sterile environment is maintained for the IDM and other portions of the surgical robotics system. In some embodiments, the junction between the mating interface 1308 and the reciprocal mating interface 1310 may further comprise a gasket to prevent fluids from penetrating the junction.

In some embodiments of the surgical drape, the surgical drape 1300 may further include a plurality of sterile adapters 1400 that provide a sterile boundary between the IDM and the outside environment or the surgical tool. In certain embodiments, the sterile adapter 1400 is configured to accommodate a rotating interface of an IDM, such as IDM 300. In the embodiment of FIG. 14, the sterile adapter 1400 comprises an outer ring 1402 and an inner disk 1404. The outer ring 1402 is connected to the sterile sheet 1302, and the inner disk 1404 is connected to the first protrusion 1304, as illustrated in FIG. 14. The inner disk 1404 is rotatably secured within the outer ring 1402. In the embodiment of FIG. 14, the sterile adapter 1400 covers the attachment interface 310 of the IDM 300 such that the sterile adapter 1400 is positioned between the attachment interface 310 and a surgical tool 500 when the surgical tool 500 is secured to the IDM 300. This configuration of the sterile adapter 1400 may allow the inner disk 1404 or the outer ring 1402 to freely rotate with the rotation of the IDM 300 and the surgical tool 500. The outer ring 1402 and the inner disk 1404 may be composed of rigid materials (e.g., metals or hard plastics). In alternate embodiments, portions of the inner disk may be a membrane that covers the plurality of torque couplers of the IDM.

Figure 15:
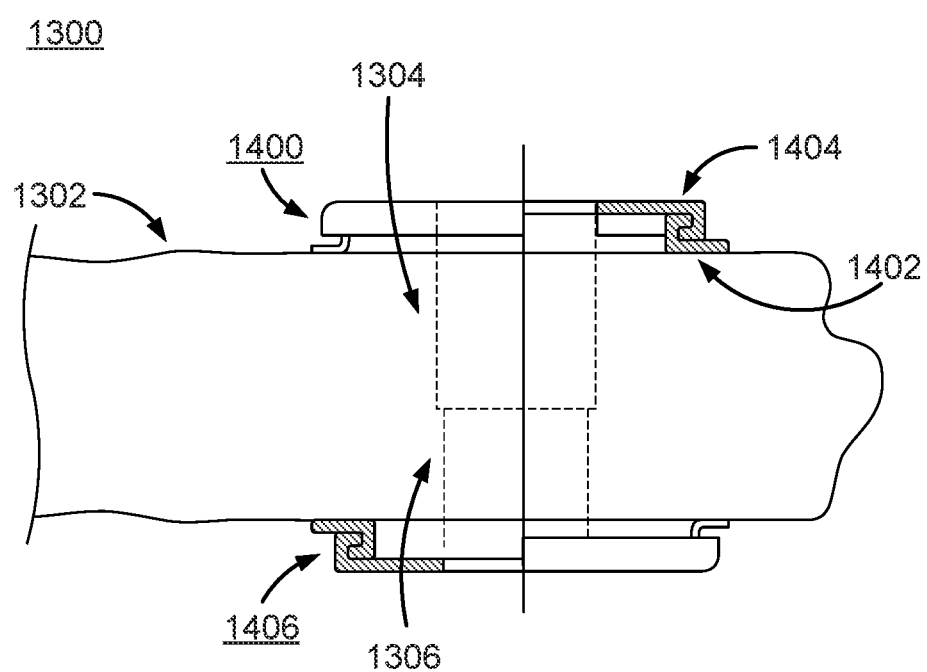
FIG. 15 illustrates a cross-sectional view of sterile adapters of a surgical drape for an instrument device manipulator, according to one embodiment.

FIG. 15 illustrates a cross-sectional view of sterile adapters of a surgical drape for an instrument device manipulator, according to one embodiment. As described in regards to FIG. 14, the surgical drape 1300 may include a plurality of sterile adapters, such as 1400 and 1406, that are configured to accommodate a rotating interface of an IDM 300. In the embodiment of FIG. 15, a sterile adapter 1400, 1406 is positioned at each end of the IDM 300. A sterile adapter 1406 that is configured to cover the end of the IDM 300 without the attachment interface 310 may vary in structure from a sterile adapter 1400 that is configured to cover the attachment interface 310, i.e., the sterile adapter may not need structures to accommodate for the plurality of torque couplers 314. In alternate embodiments, portions of the first protrusion 1304 or the second protrusion 1306 may include a rotatable component, such as a roller bearing or a similar inner disk and outer ring mechanism as previously described, such that rotation occurs within the passage 312 rather than at a sterile adapter. This configuration may improve stability during rotation of the surgical tool holder 308 due to the smaller diameter of the protrusion compared to the diameter of the inner disk 1402. This configuration may also eliminate the need for an additional sterile adapter 1406 at the end of the IDM 300 without the attachment interface 310.

Figure 16:
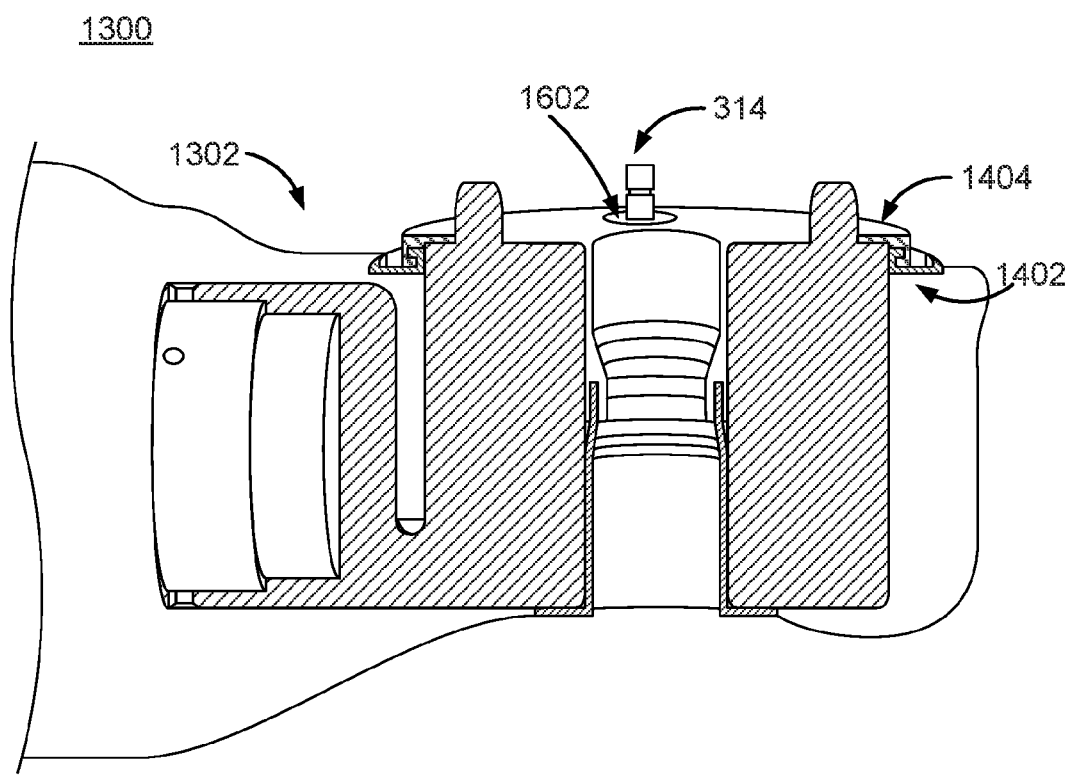
FIG. 16 illustrates a cross-sectional view of a surgical drape for an instrument device manipulator, according to an additional embodiment.

FIG. 16 illustrates a cross-sectional view of a surgical drape for an instrument device manipulator, according to an additional embodiment. As illustrated in FIG. 16, the surgical drape 1300 provides a sterile boundary for the IDM and the surgical arm. The embodiment of FIG. 16 illustrates the inner disk 1404 through which respective torque couplers 314 may protrude.

VIII. Power and Data Transmission

Figure 17:
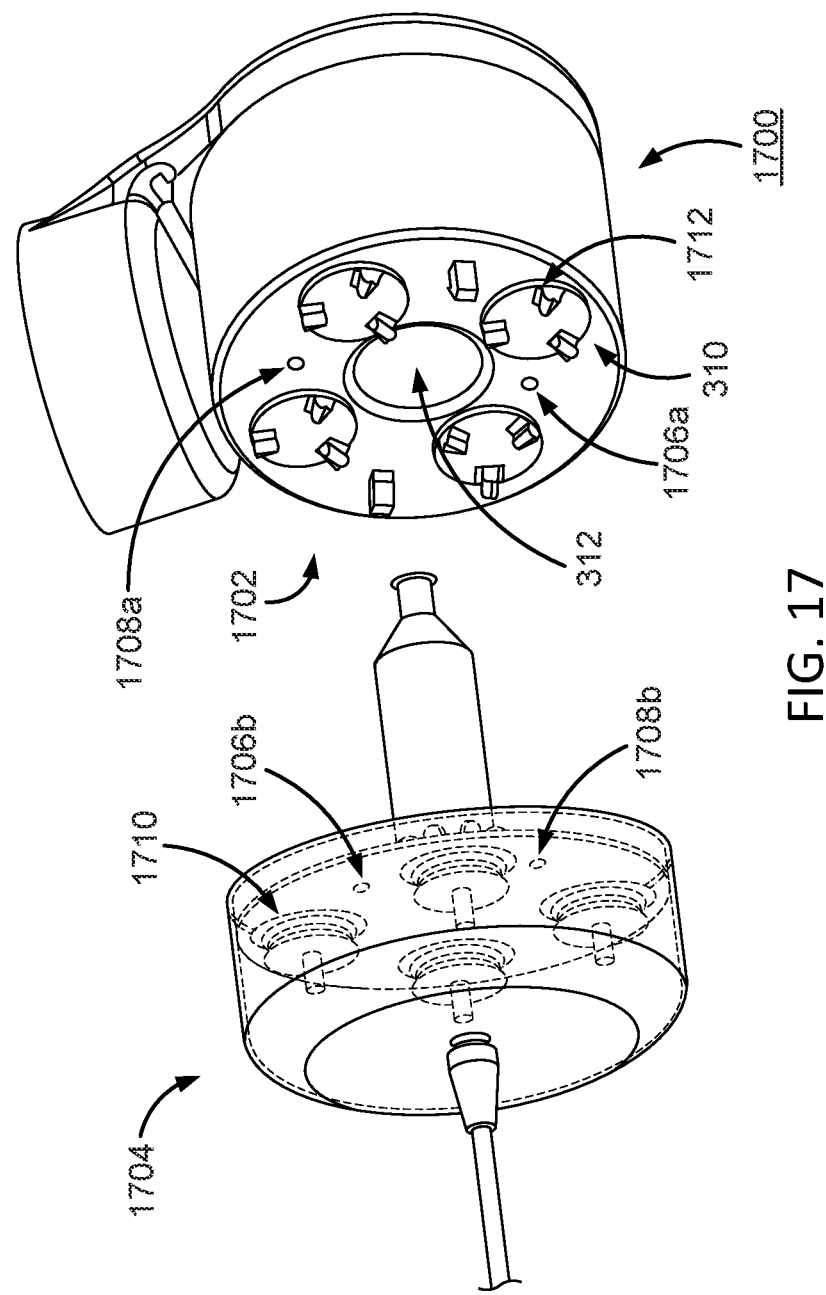
FIG. 17 illustrates an optical interface for power and data transmission between a surgical tool and an instrument device manipulator, according to one embodiment.

FIG. 17 illustrates an optical interface for power and data transmission between a surgical tool and an instrument device manipulator, according to one embodiment. In certain embodiments, surgical tools may have capabilities that require power and/or data transmission, such as a camera or a light source that operates at the proximal end of the elongated body of the surgical tool. Other features may include tracking sensors or tension sensors. Surgical tools with such features may use cable connections to the rest of the platform for power and/or data transmission and thus hinder the surgical tool's capability to roll. To achieve infinite roll for these surgical tools, power and/or data transmission may occur through inductive power and an optical interface.

In the embodiment of FIG. 17, the IDM 1700 includes a power transmitter, and the surgical tool includes a power receiver. The power transmitter inductively transmits power to the power receiver across the attachment interface 310 without the need for direct connections. In the embodiment of FIG. 17, a plurality of coils are secured within the IDM 1700 perpendicular to the attachment interface 310 and centered along the rotational axis of the IDM 1700. The coils are coupled to the integrated controller and configured to receive signals to transmit power. The coils may be of various diameters centered around the passage 312 of the IDM 1700. A larger diameter may improve the power transmission capabilities. The surgical tool 1704 may include a battery to support the instrument operation in the event that the wireless power transmission is interrupted. In some embodiments, the power transmitter may have shielding to prevent transferring heat to nearby metal components and interfering with the motors in the IDM 1700. Possible shielding materials include mu-metals.

In the embodiment of FIG. 17, the optical interface is between the mating surfaces of the IDM 1700 and the surgical tool 1704. The IDM 1700 and the surgical tool 1704 each include a plurality of optical transmitters, such as 1706a, 1706b, and a plurality of optical receivers, such as 1708a, 1708b. In the embodiment of FIG. 17, there is at least one pair for the connection between the surgical tool 1704 to the IDM 1700 for transferring data such as imaging data, and at least one pair for the connection between the IDM 1700 to the surgical tool 1704. In addition, a wireless point-to-point data connection can be used for high bandwidth communication from the IDM 1700 to the surgical robotic system. In some embodiments, the power transmitter may be an LED, which would require the sterile sheet across the attachment interface to be composed of a material transparent to the LED light. Alternate embodiments may use RFID technology or physical connections between the IDM 1700 and surgical tool 1704 for data transmission.

In some embodiments, the optical transmitters 1706 and optical receivers 1708 are symmetrically oriented with respect to the plurality of instrument inputs 1710 and the plurality of torque couplers 1712, respectively, such that the surgical tool 1704 may be attached to the surgical tool holder 1702 in any orientation. Once the surgical tool 1704 is attached to the surgical tool holder 1702, an optical transmitter 1706 of the surgical tool 1704 may be configured to transmit a signal to an optical receiver 1708. The signal can be used to determine the rotational orientation of the surgical tool 1704 with respect to the surgical tool holder 1702. Once the rotational orientation of the surgical tool 1704 has been determined, the optical data flow can be fully established and the actuators for the torque couplers 1712 can be accurately controlled.

IX. Alternative Considerations

Upon reading this disclosure, those of skill in the art will appreciate still additional alternative structural and functional designs through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context unless otherwise explicitly stated.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

What is claimed is:

1. A surgical instrument manipulation system comprising:
   a surgical arm configured to secure to a base;
   a surgical tool holder assembly comprising:
      a surgical tool holder having a first opening and a second opening, the first opening and second opening connected by a passage therethrough, and
      an attachment interface on a first end of the surgical tool holder; and
   a surgical tool comprising:
      a reciprocal attachment interface on a first face of the surgical tool,
      an attachment mechanism configured to releasably attach the reciprocal attachment interface to the attachment interface of the surgical tool holder, and
      an elongated body extending from the first face of the surgical tool, the elongated body capable of passing through the passage of the surgical tool holder and extending through the second opening when the surgical tool is attached to the surgical tool holder.

2. The system of claim 1, wherein the surgical arm is operable by a surgical robotics system.

3. The system of claim 1, wherein the surgical tool holder assembly further comprises an outer housing having a disk-like geometry.

4. The system of claim 1, wherein the surgical tool holder assembly comprises at least one motor configured to rotate the surgical tool holder relative to an outer housing.

5. The system of claim 4, wherein the passage, the elongated body of the surgical tool, and a rotational axis of the surgical tool holder assembly are co-axially aligned.

6. The system of claim 5, wherein the passage allows the elongated body of the surgical tool to continuously rotate about the rotational axis.

7. The system of claim 1, wherein the attachment interface comprises a plurality of torque couplers that protrudes outward from a surface of the attachment interface.

8. The system of claim 7, wherein the reciprocal attachment interface comprises a plurality of instrument inputs that are configured to reciprocally mate with the plurality of torque couplers.

9. The system of claim 8, wherein the drive mechanism for each torque coupler is configured to cause the torque coupler to rotate and thereby rotate the respective instrument input.

10. The system of claim 9, wherein the plurality of drive mechanisms are arranged in a ring formation around the passage.

11. The system of claim 7, wherein each of the plurality of torque couplers is coupled to a drive mechanism.

12. The system of claim 1, wherein the elongated body is one of the following: a steerable tool for endoscopic applications or a rigid tool for laparoscopic applications.

13. The system of claim 1, further comprising a surgical drape configured to create a sterile boundary between the surgical tool holder assembly and the surgical tool.

14. The system of claim 13, wherein the surgical drape comprises a sterile adapter that is positioned between the surgical tool holder and the surgical tool attached to the surgical tool holder via the attachment interface, the sterile adapter configured to rotatably secure to the surgical tool holder.

15. The system of claim 14, wherein the sterile adapter is capable of transmitting data, power, and electrical signals between the surgical tool holder and the surgical tool.

16. A method for attaching a surgical tool to a surgical tool holder assembly, the method comprising:
   passing an elongated body of the surgical tool through a passage of the surgical tool holder assembly, the surgical tool holder having a first opening and a second opening, the first opening and second opening connected by the passage therethrough;
   advancing the elongated body of the surgical tool through the passage of the surgical tool holder until an attachment mechanism of the surgical tool secures the surgical tool to the surgical tool holder assembly and a distal end of the elongated body extends through the second opening;
   operating the surgical tool using the surgical tool holder assembly;
   releasing the surgical tool from the surgical tool holder assembly; and
   removing the elongated body of the surgical tool from the passage.

17. The method of claim 16, wherein operating the surgical tool using the surgical tool holder assembly comprises rotating the surgical tool relative to an outer housing of the surgical tool holder assembly.

18. The method of claim 16, wherein the surgical tool holder assembly comprises an attachment interface that mates with a reciprocal attachment interface on the surgical tool via the attachment mechanism.

19. The method of claim 18, wherein the elongated body of the surgical tool extends from the reciprocal attachment interface of the surgical tool.

\* \* \* \* \*